US012515024B2

(12) United States Patent
Callister et al.

(10) Patent No.: US 12,515,024 B2
(45) Date of Patent: Jan. 6, 2026

(54) CEREBROSPINAL FLUID SHUNT WITH FLOW REGULATION

(71) Applicant: Azygos Vascular, Inc., Deephaven, MN (US)

(72) Inventors: Jeffrey P. Callister, Deephaven, MN (US); Benjamin Q. Callister, Deephaven, MN (US); Ryan Bauer, Plymouth, MN (US); Jacob Jaeger, White Bear Lake, MN (US)

(73) Assignee: Azygos Vascular, Inc., Deephaven, MN (US)

( * ) Notice: Subject to any disclaimer, the term of this patent is extended or adjusted under 35 U.S.C. 154(b) by 0 days.

(21) Appl. No.: 19/009,028

(22) Filed: Jan. 3, 2025

(65) Prior Publication Data

US 2025/0222241 A1 Jul. 10, 2025

Related U.S. Application Data

(60) Provisional application No. 63/618,049, filed on Jan. 5, 2024.

(51) Int. Cl.
*A61M 27/00* (2006.01)

(52) U.S. Cl.
CPC ... *A61M 27/002* (2013.01); *A61M 2202/0464* (2013.01); *A61M 2205/3334* (2013.01)

(58) Field of Classification Search
CPC ........ A61M 27/002; A61M 2202/0464; A61M 27/006; A61M 2205/3334
See application file for complete search history.

(56) References Cited

U.S. PATENT DOCUMENTS

| | | | | |
|---|---|---|---|---|
| 8,043,247 | B1 | 10/2011 | Glenn | |
| 11,278,708 | B2 | 3/2022 | Heilman et al. | |
| 2004/0176743 | A1* | 9/2004 | Morris .............. | A61M 25/0075 604/537 |
| 2006/0224102 | A1* | 10/2006 | Glenn ................. | A61M 27/006 604/8 |
| 2007/0112291 | A1 | 5/2007 | Borgesen | |
| 2020/0376239 | A1 | 12/2020 | Heilman et al. | |
| 2024/0115842 | A1 | 4/2024 | Malek et al. | |

* cited by examiner

*Primary Examiner* — Susan S Su
*Assistant Examiner* — Erin A Kim
(74) *Attorney, Agent, or Firm* — McAndrews, Held & Malloy, Ltd.

(57) ABSTRACT

According to embodiments, a cerebrospinal fluid (CSF) shunt includes: an inlet configured to receive CSF from a spinal intradural space in a patient; a shunt body with a sidewall and a lumen within the sidewall, wherein the shunt body is configured to extend through an interstitial space and a vein wall, wherein the lumen is in fluid communication with the inlet; and a regulator outside of the lumen, wherein the regulator is configured to regulate a flow of the CSF from the inlet by passing a regulated portion of the CSF from the lumen and into a venous system of the patient.

18 Claims, 12 Drawing Sheets

CEREBROSPINAL FLUID SHUNT WITH FLOW REGULATION

CROSS REFERENCE TO RELATED APPLICATIONS

This application claims priority to and the benefit of U.S. Prov. No. 63/618,049, filed on Jan. 5, 2024, the entirety of which is incorporated by reference herein.

BACKGROUND

Generally, this application relates to shunts for cerebrospinal fluid (CSF).

Figure 1A:
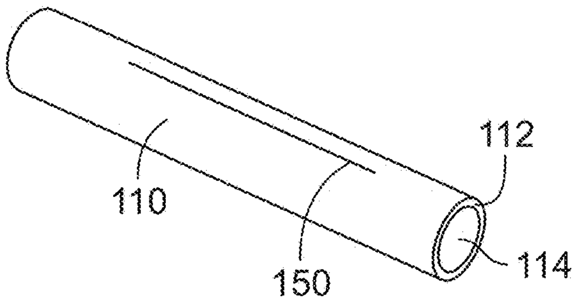
FIGS. 1A, 1B, 1C, and 1D illustrate CSF shunt bodies with different configurations for flow regulation, according to embodiments.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

SUMMARY

According to embodiments, a CSF shunt includes: an inlet configured to receive CSF from a spinal intradural space in a patient; a shunt body with a sidewall and a lumen within the sidewall, wherein the shunt body is configured to extend through an interstitial space and a vein wall, wherein the lumen is in fluid communication with the inlet; and a regulator outside of the lumen, wherein the regulator is configured to regulate a flow of the CSF from the inlet by passing a regulated portion of the CSF from the lumen and into a venous system of the patient. The regulator may be a slit regulator in the sidewall of the shunt body. The sidewall of the shunt body may include a first region including a first material and a second region including a second material; at least one of the first material has a lower durometer than the second material, or the first region has a smaller inner diameter than the inner diameter of the second region; the regulator is in the first region; and no regulator is in the second region. The first material may have a lower durometer than the second material. The regulator may include a non-stick material. The first region may have a smaller inner diameter than the inner diameter of the second region. The first material may have a lower durometer than the second material and the first region has a smaller inner diameter than inner diameter of the second region. The regulator may include a first regulator and a second regulator; the sidewall of the shunt body may include a first region including a first material and a second region including a second material; at least one of the first material may have a lower durometer than the second material, or the first region has a smaller inner diameter than the inner diameter of the second region; the first regulator may be in the first region; and the second regulator may be in the second region. The first material may have a lower durometer than the second material. The first regulator and the second regulator may include a non-stick material. The first region may have a smaller inner diameter than the inner diameter of the second region. The first material may have a lower durometer than the second material and the first region may have a smaller inner diameter than the inner diameter of the second region. The first regulator and the second regulator may regulate differently from each other. The regulator may include at least one discontinuity in the sidewall of the shunt body and a sleeve exterior to an outer surface of the sidewall of the shunt body, wherein the sleeve overlaps the at least one discontinuity. The sleeve may include an end coupled to the shunt body and an end at least partially not coupled to the shunt body. The end at least partially not coupled to the shunt body may be entirely not coupled to the shunt body. The sleeve may include at least one discontinuity.

According to embodiments, a CSF shunt includes: an inlet configured to receive CSF from a spinal intradural space in a patient; an outlet configured to provide the CSF into a venous system in the patient; a shunt body with a sidewall and a lumen within the sidewall, wherein the shunt body is configured to extend through an interstitial space and a vein wall, wherein the lumen is in fluid communication with the inlet and the outlet, such that a flow of the CSF flows between the inlet and the outlet; and a regulator configured to vary at least one of the size or the shape of the outlet to regulate the flow of the CSF fluid. The shunt body may include a first region including a material having a first durometer and a second region including a material having a second durometer less than the first durometer; and the outlet may be formed at least partially by the second region.

According to embodiments, a CSF shunt includes: an inlet configured to receive CSF from a spinal intradural space in a patient; an outlet configured to provide the CSF into a venous system in the patient; a shunt body with a sidewall and a lumen within the sidewall, wherein the shunt body is configured to extend through an interstitial space and a vein wall, wherein the lumen is in fluid communication with the inlet and the outlet, such that a flow of the CSF flows between the inlet and the outlet; and a constrictor positioned outside of the shunt body, wherein an inner diameter of the constrictor is less than an outer diameter of the shunt body, wherein the constrictor is elastic and regulates the flow of the CSF.

DETAILED DESCRIPTION

Embodiments herein relate to systems and methods for draining excess CSF from a patient's subarachnoid space, and particularly the subarachnoid space in the thecal sac of the spinal canal. Such CSF shunts and deployment techniques are described in U.S. Prov. No. 63/446,064, filed on Feb. 16, 2023, and U.S. Ser. No. 18/443,455, filed on Feb. 16, 2024, the entireties of which are incorporated by reference, herein. Embodiments herein describe CSF shunts with flow regulation features. CSF shunts are described, but the principles may be applicable to other types of shunts, such as interatrial/interventricular shunts, pulmonary artery shunts, or other arterial/venous shunts.

Cerebrospinal fluid is an ultrafiltrate of blood plasma. It is a substantially clear liquid with a density close to that of water. The CSF bathes the brain inside the skull as well as the spine and spinal nerve roots inside the spinal canal. The CSF is enclosed within the dura mater or dura, which is a thick and relatively inelastic membrane covering the inner surface of the skull and spinal canal. In the spinal area the dura is called the thecal sac. The CSF is secreted inside the brain ventricles by the choroid plexus, and it circulates around the folds of the brain and around the spinal cord and nerve roots. The CSF is reabsorbed into the venous blood by the arachnoid granulations. Some arachnoid granulations are located around the brain along the walls of the venous sinuses, in which case the CSF transits into the venous sinuses. Other arachnoid granulations are located along the nerve roots of the spinal canal, in which case the CSF transits into the veins surrounding the nerve roots.

Hydrocephalus is a relatively neurological disease in which, for various reasons, the pressure of the CSF increases. Hydrocephalus can be communicating, where the CSF flow pathway is not interrupted but there is a deficit of the reabsorption of CSF by the arachnoid granulations. Hydrocephalus can also be caused by overproduction of CSF. Hydrocephalus can be secondary to an obstacle to the CSF circulation, which is called non-communicating hydrocephalus. Some hydrocephalus conditions are congenital, while others may be acquired (for example, after subarachnoid hemorrhage).

One approach to treating hydrocephalus is by diverting CSF. CSF diversion is commonly known as shunting and refers to the placement of a permanently (or semi-permanently) implanted shunt (e.g., a tube) that diverts CSF from the subarachnoid space to another area of the body where it can be reabsorbed. This surgery may be performed by neurosurgeons.

In addition to hydrocephalus, there are other diseases that also be treated by CSF diversion using the techniques described herein. For example, in some patients, brain ventricles may be contracted, resulting from a disease such as idiopathic intracranial hypertension (IIH). In some patients, ventricles may be enlarged while CSF pressure has not increased, resulting in a disease such as normal pressure hydrocephalus (NPH).

Conventional shunts may access the CSF via locations in the skull. However, the neurosurgery required to implant such shunts may be relatively risky. For example, when a shunt is to be positioned in an inferior petrosal sinus, such a procedure may have high risks and a failure could lead to a neurological complication or even death. Embodiments disclosed herein describe a delivery system and CSF shunt for placement outside of the cranial cavity. Particularly, embodiments herein disclose placing a CSF shunt in the spinal canal—e.g., in the lumbar region. The lumbar region includes multiple sites that can be accessed via endovenous catheters guided by X-ray fluoroscopy to deliver and position the CSF shunt. The spinal region (e.g., lumbar region) may be a safer region to operate on and present lower risk, as opposed to brain surgery.

Notably, CSF shunts may fail at a relatively high rate (e.g., more than 50% over two years, and even larger percentages over longer periods of time). Further, when CSF shunts fail and otherwise need to be removed and/or replaced, the spinal region may again be a safer region (as compared to the cranial region) to perform a procedure, such as an endovenous procedure.

Considering at least Poiseuille's law (Eq. 1) and Orifice flow (Eq. 2), the shunt ID (circular profile) may be on the order of 0.001" to 0.005" if no dedicated flow constriction or valve is present, lending itself to potential occlusion from clotting or protein build up. For example: with Equation 1, taking a shunt tube inner diameter of 0.005" in with a change in pressure of 10 cm/H2O at a shunt length of 4 centimeters, the volumetric flow rate is calculated to be 13 ml/h or 213 ml/day. This is the idealized scenario ignoring surface effects from the shunt that could further reduce the flow rate. For Equation 2 even when taking the idealized case and disregarding the Coefficient of Discharge with a simple, flow regulation orifice diameter of 0.005" the flow rate may be calculated to be 63 ml/h or over 1,500 mL/day, which may be too large.

$$Q=\pi*\Delta p*r*48*\mu*l \qquad \text{Eq 1.}$$

Where Q is flow rate, p is change in pressure over length of shunt tube, r is radius of pipe, u is dynamic viscosity, and l is length of shunt tube.

$$Q=\mathrm{Cd}*A*\sqrt{(2*g*H)} \qquad \text{Eq 2.}$$

Where Q is flow rate, Cd is Coefficient of Discharge, A is area of orifice, g is gravitational constant, and His head pressure.

Conventional shunts in the lumbar region that drain into the abdominal cavity may become kinked and obstructed when the lower spine moves. This poses a difficulty in isolating the shunt body and maintaining a tube opening amidst body movements.

As used herein, distal is defined as furthest from the doctor's hand during deployment of the shunt, and proximal as closest to the doctor's hand.

Embodiments disclosed herein relate to CSF shunts with regulators to regulate CSF flow through the shunt. Such flow may be 25-350 ml/day, or for example, approximately 250 ml/day. A regulator in a CSF shunt can include one or more individual regulators which work together to provide an overall flow regulation for the CSF shunt. Regulation may enable greater flow of CSF through the regulator when the CSF is at a higher pressure and enable a lesser flow of CSF through the regulator when the CSF is at a lower pressure. When the CSF pressure is sufficiently low, the regulator may close altogether, thereby preventing flow of fluid through the regulator. When the regulator closes, blood from the venous system is prevented from flowing back through the shunt and towards the intradural region.

Figure 11:
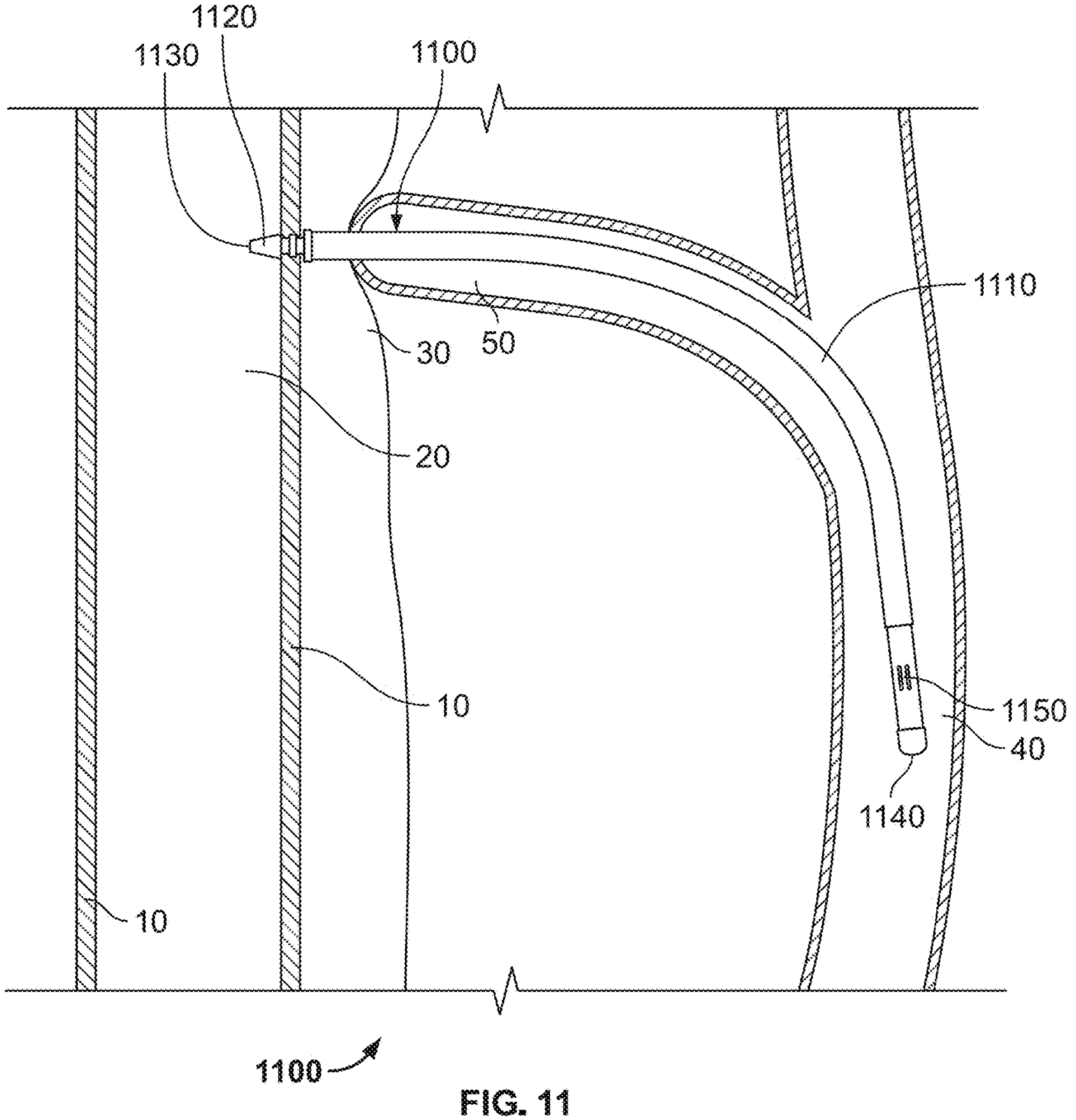
FIG. 11 shows a CSF shunt deployed in a patient, according to embodiments.

Turning to FIG. 11, a CSF shunt 1100 is deployed in a patient, according to embodiments. The exemplary CSF shunt 1100 has a shunt body 1110, a distal portion 1120, an inlet 1130, a closed end 1140, and a regulator 1150. The patient's anatomy includes dura 10 (in the spinal column, also called the thecal sac), intradural space 20, interstitial space 30, ascending lumbar vein 40, and intervertebral (or foraminal) vein 50. CSF resides in the intradural space 20, whereas blood resides in the ascending lumbar vein 40 and the intervertebral vein 50. There is a pressure differential between the CSF in the intradural space 20 and the blood in the veins 40, 50. This pressure differential can vary over time. Generally, the pressure of the CSF in the intradural space 20 is greater than the pressure of the blood in the veins 40, 50. The CSF shunt 1100 provides a fluid path between these regions such that the CSF can flow from the intradural space 20 into the veins 40, 50.

The inlet 1130 of the CSF shunt 1100 is positioned in the intradural space 20 and receives an inflow of CSF. As shown, the inlet 1130 is in the distal portion 1120 of the CSF shunt 1100, which is coupled on its other side with the shunt body 1110. The inlet 1130 may optionally be on the shunt body 1110, for example, if there is no distal portion 1120. The distal portion 1120 may be used to facilitate implantation of the CSF shunt 1100 through the dura 10. Such implantation techniques are described with respect to FIGS. 6A-6C. Other implantation techniques useable with the shunts described herein are described in U.S. Prov. No. 63/446,064, filed on Feb. 16, 2023, and U.S. Ser. No. 18/443,455, filed on Feb. 16, 2024, the entireties of which are incorporated by reference herein.

The closed end 1140 of the CSF shunt 1100 is positioned in the ascending lumbar vein 40, although it could be positioned in the iliac vein, the azygos vein, or any suitable location in the patient's venous system. The closed end 1140 may be a cap, a seal, or integrated into other portions of the CSF shunt 1100, such as the shunt body 1110.

The shunt body 1110 is interposed between the inlet 1130 and the closed end 1140. The shunt body 1110 includes a sidewall and a lumen. The shunt body 1110 may include a material such as implantable polymer(s) such as Polyurethane, Polyureathane-copolymers, silicone, a braided composite of polymers, radiopaque markers, a composite of polymers, and/or polymer(s) with a durometer ranging from 60 A to 65 D. The shunt body 1110 may include multiple regions with differing materials or physical properties or may be one uniform region. As shown, the shunt body 1110 includes two regions. Other examples of a shunt body with multiple regions are shown in FIGS. 3A, 3B, 5A, and 6A, which will be further described.

The regulator 1150 is located on the sidewall of the shunt body 1110 and extends from the exterior surface of the shunt body 1110 to the lumen. The lumen is in fluid communication with the inlet 1130 and the regulator 1150, such that CSF can flow therebetween. The CSF flow through the lumen is regulated by the regulator 1150, which passes or provides a regulated amount of CSF into the patient's venous system (in the example shown, ascending lumbar vein 450).

Turning to FIGS. 1A-1D, different embodiments of a shunt body 110 are illustrated. The shunt body 110 may be similar to the shunt body 1110. The shunt body 110 may be part of a larger shunt, such as the one shown in FIG. 11. The shunt body 110 is shown as having two open ends, but one end could be closed, forming a closed end similar to the closed end 1140. The other end of the shunt body would still be open to allow fluid communication with the inlet (or form the inlet itself) that receives the CSF from the patient's intradural space.

The shunt body 110 includes a sidewall 112 and a lumen 114. The lumen 114 may be formed by the sidewall 112, as illustrated. The lumen 114 is in fluid communication with the inlet. In an embodiment, the sidewall 112 defines the inlet.

The shunt body 110 (or the shunt itself) may have a length of between 0.5 to 20 cm, such as approximately 5 cm. The sidewall 112 may have an inner diameter of between 0.1 to 1.6 mm, such as approximately 0.5 mm. The sidewall 112 may have an outer diameter of between 0.2 to 2.6 mm, such as approximately 1.27 mm. The sidewall 112 may have a thickness of between 0.05 and 0.38 mm, such as approximately 0.25 mm. The sidewall 112 may be a composite. An example of a composite includes a sidewall 112 with multiple concentric layers. Each layer may include a different material than adjacent layer(s). Such exemplary materials are described above with respect to the shunt body 110. An example of such a composite sidewall 112 includes an outer layer including, e.g., polyurethane 45D and an inner layer including, e.g., 60A polyurethane loaded with PTFE. The outer layer may be made of a higher durometer material and a molecularly different polyurethane to both moderate flow through the discontinuity along with enhancing, as an example, anticlotting impregnation in the material. The inner layer may be made of a lower durometer material to maintain flexibility in the shunt and to be both lubricous to easily accommodate sliding over a positioning wire and help inhibit protein build up. In another embodiment, there may further be an intermediate layer. The intermediate layer may be added, e.g., to strengthen the wall to prevent crushing, to enhance and/or decrease flexibility, to dampen the rate the in which the flow regulator opens, and/or to aid in bonding the inner layer to the outer layer.

A regulator 150 is further shown. The regulator 150 may be similar to the regulator 1150. The regulator 150 selectively allows a regulated portion of CSF to flow from the lumen 114 and into the venous system of the patient.

In the embodiments of FIGS. 1A-1D, the regulator 150 includes a discontinuity in the sidewall 112. The depicted discontinuities are slits. Although only one discontinuity is shown in each of FIGS. 1A-1D, a regulator 150 can have multiple discontinuities, such as multiple slits. As used herein, "discontinuity" includes multiple discontinuities in a regulator 150, whether connected or not, as will be understood. The discontinuities extend from the exterior surface of the sidewall 112, through the sidewall 112, and to the lumen 114. The discontinuity may have a constant cross-sectional shape (including width) as it extends across the entirety of the sidewall 112, or the cross-sectional shape of the discontinuity may vary across the depth of the sidewall 112.

The discontinuity may be formed mechanically by puncturing or otherwise moving a cutting device (e.g., scalpel, razor blade, etc.) across the thickness of the sidewall 112. The discontinuity may be cut by a laser. According to a technique, the discontinuity may be formed by a mold, such that the shunt body 110 includes the discontinuity when it is removed from the mold. According to another technique, an embedded material, such as a non-stick material, may be used to impart the discontinuity in the sidewall. The shunt body 110 may be cast or otherwise first formed with the embedded material embedded therein. Subsequently, the embedded material is removed to impart the discontinuity.

The discontinuity (e.g., slit) can run longitude and or radially or a combination thereof along the shunt body 110. A discontinuity (or multiple discontinuities) may be imparted anywhere along the shunt body 110 that will be in the patient's venous system when the shunt is implanted. For example, the discontinuity (or discontinuities) may be located proximally along the shunt body 110. The slits maybe coated, and or impregnated with anti-clotting and or anti-microbial coatings. A given discontinuity, such as a slit, may have a length of between 0.5 to 4 mm, such as approximately 2.5 mm.

In the case of a slit, it may only open when the CSF pressure exceeds a predetermined pressure by causing the shunt body 110 to radially expand and cause the slit to open.

The sidewall 112 includes an elastic material and/or semi elastic material, such as polyurethane or silicone. When CSF pressure builds up in the lumen 114, the sidewall 112 expands. The inner diameter and/or outer diameter of the sidewall 112 increases. This causes the discontinuity of the regulator 150 to open. The greater the pressure, the greater the expansion, the greater the amount that the discontinuity opens, and the greater the amount of CSF fluid is diverted through the opened discontinuity. The effect of diverting a variable amount of CSF fluid through the regulator 150 in response to a variable pressure of the CSF fluid in the lumen 114 allows the discontinuity-type (or slit-type) regulator 150 to regulate the flow of CSF between the patient's intradural space and the venous system.

Figure 1B:
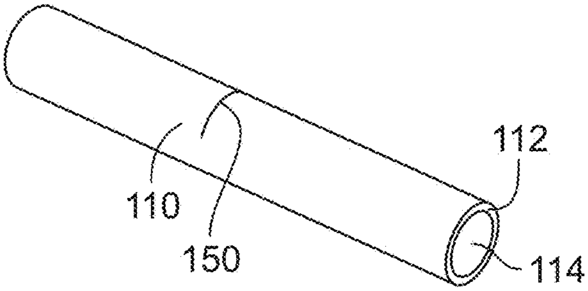
Figure 1C:
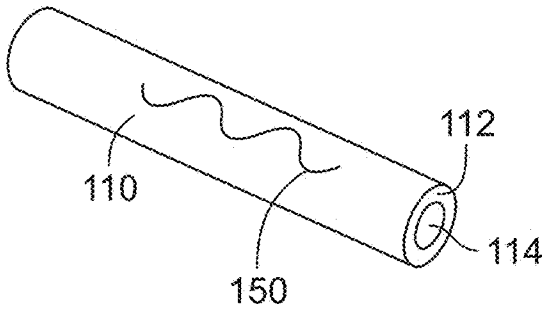
Figure 1D:
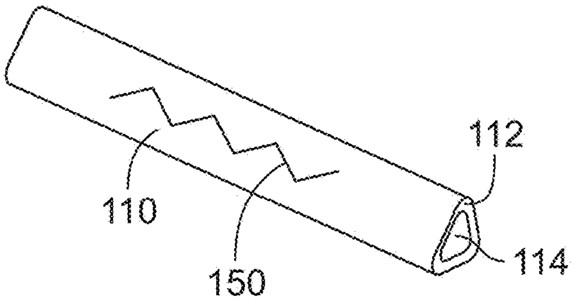

As shown in the examples of FIGS. 1A-1D, the shunt body 110 (and sidewall 112 and lumen 114) can have different shapes and thicknesses. Further as shown, the regulator 150 can have differently-shaped discontinuities. In FIG. 1A the discontinuity is a straight slit that extends along a portion of the length of the shunt body 110. In FIG. 1B, the discontinuity is a straight slit that extends radially around a portion of the shunt body 110. In FIG. 1C, the discontinuity is a wavy slit (e.g., sinusoidal) that extends along a portion of the length of the shunt body 110. Further, the thickness of the sidewall 112 is greater than that in FIGS. 1A and 1B. A thicker sidewall 112 may have a thickness of between 0.15 and 0.5 mm, as opposed to a thinner sidewall 112, which may have a thickness of between 0.025 and 0.25 mm. In FIG. 1D, the sidewall 112 has a triangular cross-sectional profile (instead of circular as shown in FIGS. 1A-1C). Other cross-sectional profiles of the sidewall 112 are considered, such as square, rectangular, pentagonal, hexagonal, elliptical, irregular, or the like. Also in FIG. 1D, the discontinuity is a triangular wave. While FIGS. 1A-1D show some examples, the specifics of a given shunt body 110 or regulator 150 can vary according to the embodiments described herein. Further, although the regulators 150 in FIGS. 1A-1D have only one discontinuity, they may have multiple discontinuities, such as two, three, or more discontinuities.

Various factors may influence the radial expansion of the shunt body 110 that will determine when and how much the regulator 150 will open. Some of these factors include: the discontinuity length or shape in the regulator 150 (e.g., a longer slit can open at a lower pressure); the durometer of the shunt body 110 (a lower durometer expands easier, and shunt body 110 durometers can range from approximately 35 A up to 55 D); the thickness of the sidewall 112 (a thicker sidewall 112 takes more pressure to radially expand; the inner diameter of the sidewall 112 (smaller diameter requires more head pressure to cause expansion); and/or shunt body 110 cross-sectional shapes (oval, triangular, or other shunt body 110 shapes effect the control opening/closing mechanism of the regulator 150, for example with a specific orientation). These factors relate to the ability of the shunt body 110 to expand radially outward (sometimes referred to hoop strength/stress and/or radial force, and here also inclusive of non-round tube) per a given internal CSF head pressure and an external venous pressure. These elements all combine to define the radial force applied to the shunt body 110. The regulator 150 may activate (i.e., the discontinuity expands and opens) from a predetermined head pressure ranging from approximately 2 cmH2O up to approximately 15 cmH2O when the subarachnoid, intradural CSF pressure is greater than the venous pressure.

Examples of a lower durometer material for the shunt body 110 includes a material with a durometer from 15 A to 90 A, such as approximately 80 A, for example. Examples of a higher durometer material includes a material with a durometer from 35 D to 75 D, such as approximately 55 D, for example. Implantable silicones and some urethanes are examples of materials in the lower durometer grades. Implantable silicones from 15 A up to 40 D and urethanes may range from the 60 A up to 70 D.

When the differential between the CSF in the subarachnoid, intradural space and the intravenous region drops, for example, within the opening pressure at the lower range of the radial force (e.g., at or below 5 cm H2O), the shunt body 110 will constrict back to its original shape and the discontinuity will collapse and close. Thus, the regulator 150 can inhibit regress of blood from the venous system into the shunt body 110.

When the CSF pressure increases, the discontinuity will open accordingly more giving more outflow. This is influenced the shunt body 110 parameters discussed above, and the discontinuity act as a flow regulator.

The discontinuity(ies) opening and closing pressure may be influenced by the radial force applied on the shunt body 110. The configuration of the discontinuity (e.g., shape, orientation) may be selected in view of the factors discussed above. Many of the factors described above can be adjusted and may be combined with other design details to impart the desired slit opening pressure and flow regulation. As another example, the sidewall 112 in the region of the regulator 150 may be thinner to impart a lower opening pressure for the discontinuity, or the shunt body 110 can contain irregular and varying geometry (i.e., molded features in the tubing and/or on the inner or outer surface(s) of the sidewall 112) along its length to tailor specific mechanical properties. As discussed above, the sidewall 112 can include a composite material. As further explained above, such layer(s) can, for example, act as dampening mechanism for regulating pressure. In addition, each one of the aforementioned factors can be controlled on any specific segment of the shunt body 110 length to produce the desired regulation by the regulator 150.

Figure 2A:
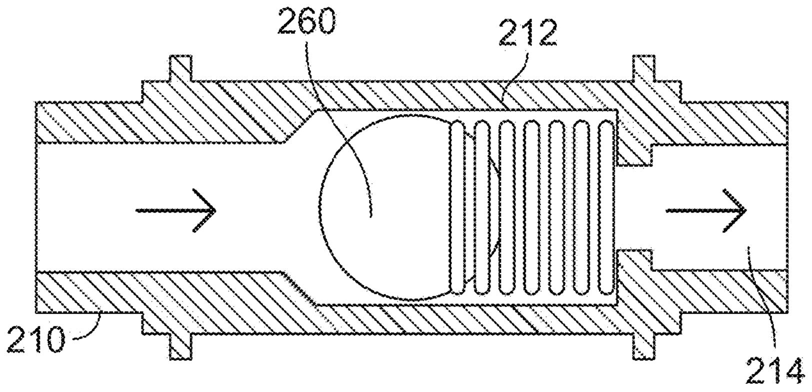
FIGS. 2A and 2B illustrate a CSF shunt body with an internal mechanical valve for flow regulation, according to embodiments.
Figure 2B:
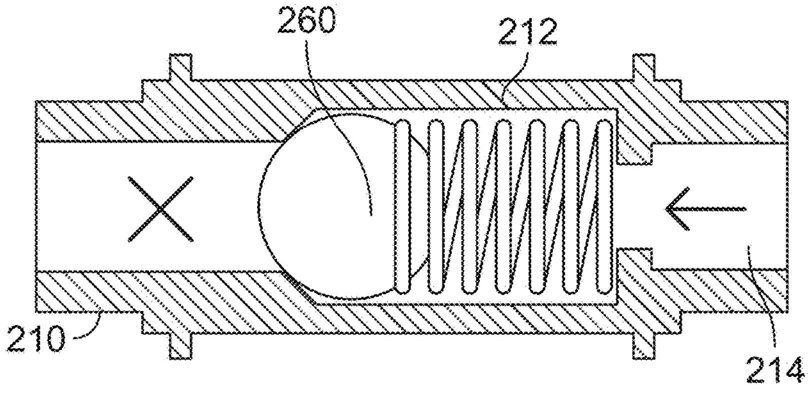

As shown in FIGS. 2A and 2B, a shunt body 210 (similar to shunt body 110) includes a sidewall 212 and a lumen 214. A mechanical valve 260 can be positioned within the lumen 214 that can control flow and back flow. In FIG. 2A, the mechanical valve 260 allows CSF to flow from the intradural space to the venous region. In FIG. 2B, the mechanical valve 260 prevents back flow of blood from the venous region into the intradural space. A regulator such as regulator 150 (not shown) may be incorporated into the shunt body 210.

Figure 3A:
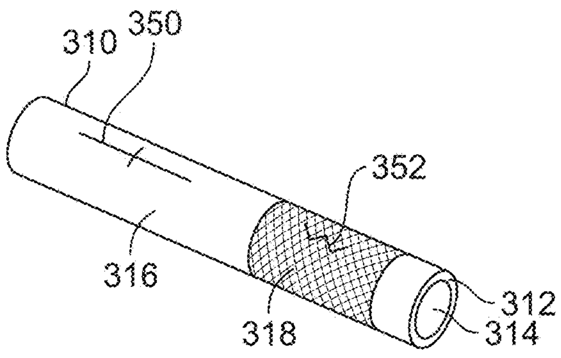
FIGS. 3A and 3B illustrate CSF shunt bodies with examples of different flow regulators, according to embodiments.
Figure 3B:
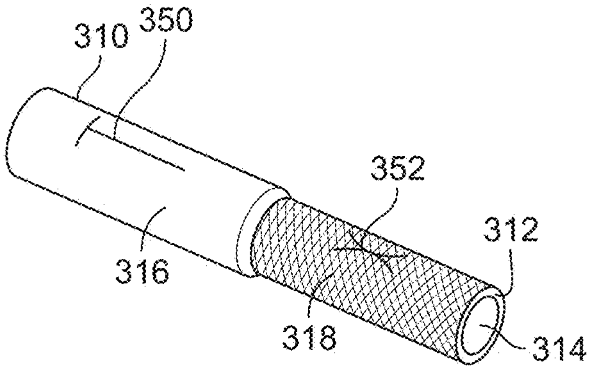

FIGS. 3A and 3B illustrate embodiments of a CSF shunt body 310, with examples of different regulators 350, 352, according to embodiments. As will be understood, the shunt body 310 may be similar in regard to shunt bodies 110, 210, and regulators 350, 352 may be similar in regards to regulator 150. As shown, the regulators 350, 352 have slit-type discontinuities. In FIG. 3A, the shunt body 310 includes a first region 316 connected or integrated with a second region 318. The first region 316 may have a regulator 350, such as one with one or more discontinuities as with regulator 150. The second region 318 may have a regulator 352, such as one with one or more discontinuities as with regulator 150. In an embodiment, the second region 318 has regulator 352, but there is no regulator in the first region 316. In an embodiment, the first region 316 has a regulator 350, but there is no regulator in the second region 318.

The second region 318 may have a lower or greater durometer than the first region 316. In the second region 318, the sidewall 312 may have a smaller or larger inner diameter than the sidewall 312 has in the first region 316. According to embodiments, the lower durometer and/or greater inner diameter region of the sidewall 312 may include a regulator, while the higher durometer and/or lesser inner diameter may not include a regulator. According to an embodiment, the inner diameters between the first region 316 and the second region 318 vary while having the sidewall 312 as a single integrated component.

In another example, the first region 316 of the sidewall 312 has a first cross-sectional shape (e.g., circular), and the second region 318 of the sidewall 312 has a second cross-sectional shape (e.g., semi-triangular, having rounded corners). In the case of a semi-triangular cross-sectional shape, the second region 318 of the sidewall 312 may have regulator(s) on the flat sections or the rounded corners. The thickness of the sidewall 312 may differ in the first region 316 and the second region 318.

According to some embodiments, the regulator(s) 350, 352 may have multiple discontinuities in parallel or that cross or intersect (e.g., X or Y shaped) or have some other spatial relationship with each other.

Figure 4A:
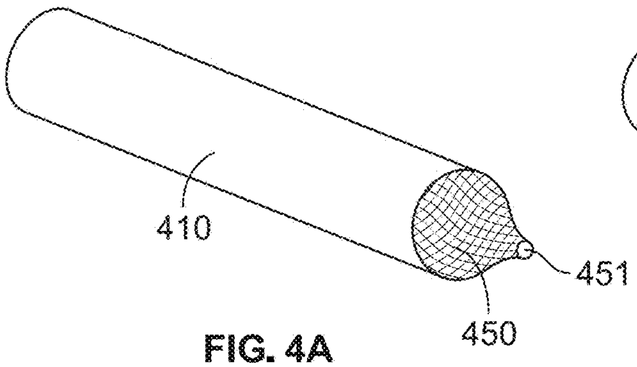
FIGS. 4A and 4B illustrate CSF shunts with different configurations for flow regulation, according to embodiments.
Figure 4B:
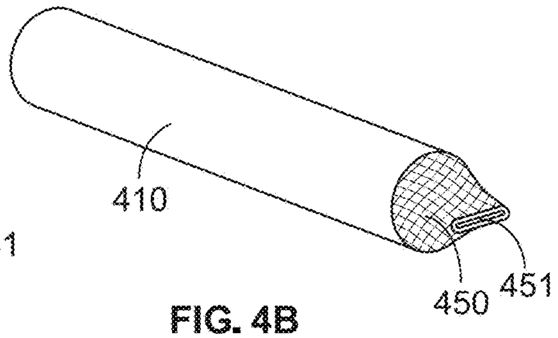

FIGS. 4A and 4B illustrate embodiments of a CSF shunt body 410 with different configurations for flow regulation. The shunt 400 includes a shunt body 410, which may be similar to shunt bodies 110, 210, 310 in respects. Instead of having a cap or sealed end, however (as with shunt 1100), the shunt body 410 is connected to or integrated with a regulator 450, which includes or defines an outlet 451. The regulator 450 may be similar in respects to regulators 150, 350, 352. The outlet 451 in the regulator 450 may be slit(s) or another type of aperture. The regulator 450 is configured to be positioned in the patient's venous system to allow outflow of CSF therein. The regulator 450 may have various shapes (e.g., conical nose, duckbill shape, bullet shape, pyramidal shape, square, a tube that unravels (like a party blowout noisemaker), or the like). The regulator 450 may include or be made of a low durometer material, such as an elastomeric material. The material of the regulator 450 may have a lower durometer than that of the shunt body 410. The regulator 450 may elastically expand or collapse in response to CSF pressure, thereby varying the size and/or shape of the outlet 451. The outlet 451 may responsively open or close at defined pressures. For example, the outlet 451 may be in a closed position when the CSF head pressure is below a defined pressure. The outlet 451 may open or close by varying degrees in response to higher or lower CSF pressure, respectively. The regulator 450 may be implemented with one or more additional regulators in the shunt, such as the regulators disclosed herein.

Figure 5A:
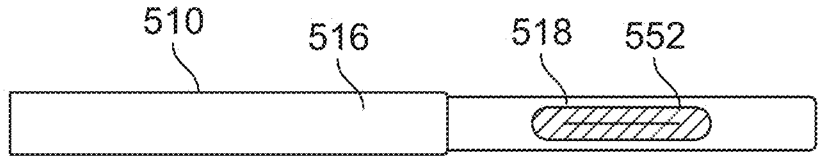
FIGS. 5A, 5B, 5C, and 5D illustrate different views of a CSF shunt body with a flow regulator, according to embodiments.
Figure 5B:
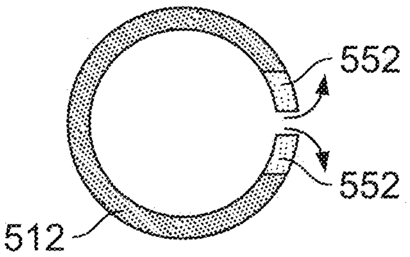
Figure 5C:
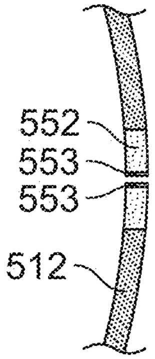
Figure 5D:
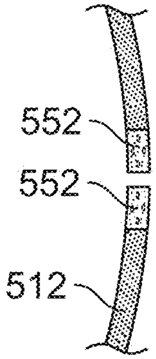

FIGS. 5A, 5B, 5C, and 5D illustrate different views of a CSF shunt body 510 with a flow regulator 552, according to embodiments. FIGS. 5B, 5C, and 5D are cross-sectional views of embodiments of the shunt body 510. The shunt body 510 may be similar to shunt bodies 110, 210, 310, 410 in respects. The shunt body 510 has a sidewall 512 and a lumen (not fully shown). The shunt body 510 can include a first region 516 (similar to the first region 316 in respects) and a second region 518 (similar to the second region 318 in respects). As depicted in FIG. 5A, a regulator 552 is included in the second region 518, although a regulator could be included in the first region 516 as well, or only in the first region 516.

The regulator 552 may be similar to regulators 150, 350, 352 in respects. In the examples shown, the regulator 552 includes a discontinuity (a slit as shown). The regulator 552 can include a radial section of the sidewall 512 (for example, a semi half circle). The regulator 552 can be cast and integrated into the sidewall 512. The regulator 552 may include or be formed of a different material than other portions of the sidewall 512. Such configurations may be similar to those described with respect to FIGS. 4A and 4B, with the shunt body 410 formed of or including a first type of material (e.g., a higher durometer material) and the regulator 450 formed of or including a second type of material (e.g., a lower durometer material).

As shown in FIG. 5C, a non-stick material 553 (e.g., a thin film PTFE, HDPE, highly-loaded PTFE polymer, or the like) can be included in the regulator 552. The non-stick material 553 may surround all or parts of the exterior of the discontinuity in the regulator 552. In such a configuration, opposing sides of the discontinuity in the regulator 552, when in a closed configuration, will not stick together.

FIG. 5D shows an embodiment when a non-stick material 553 is embedded or otherwise formed in the regulator 552 (e.g., during casting). In such a configuration, opposing sides of the discontinuity in the regulator 552, when in a closed configuration, will not stick together. Some examples of such a material for a regulator 552 include silicone PTFE, urethane, or an implantable plastic with a high loading of PTFE powder. Such materials may not substantially stick to each other even after a relatively long usage time (e.g., 4 or more years in situ).

Figure 6A:
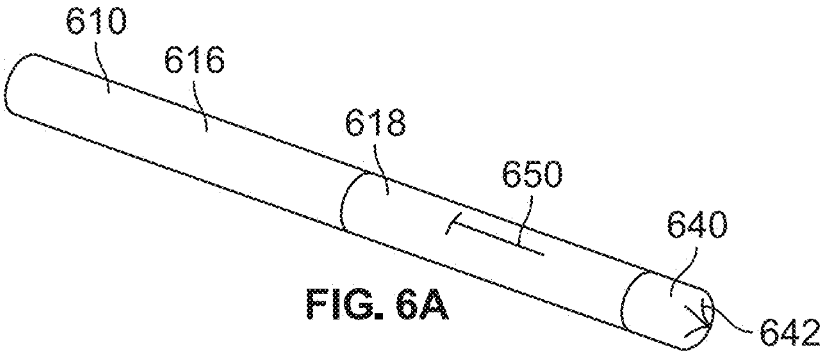
FIGS. 6A, 6B, and 6C illustrate a CSF shunt body and an end with a sealable discontinuity, according to embodiments.
Figure 6B:
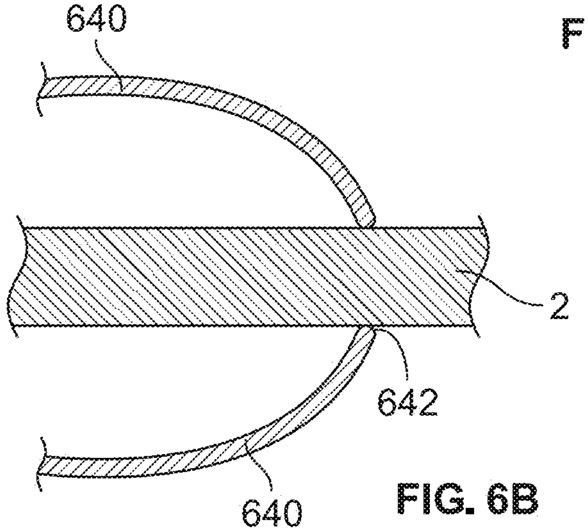
Figure 6C:
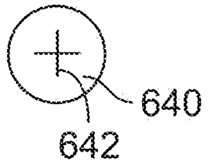

FIGS. 6A, 6B, and 6C illustrate a shunt body 610 and an end 640 with a sealable discontinuity 642, according to embodiments. The shunt body 610 may be similar to other shunt bodies described herein. As shown in FIG. 6A, the shunt body 610 includes a first region 616 and a second region 618, which includes a regulator 650 (the example being a T-shaped discontinuity). The end 640 may be similar to the closed end 1140, with the exception of the addition in end 640 of sealable discontinuity 642. In the example shown, the discontinuity 642 includes a cross that extends through the thickness of the end 640. The end 640 may include a material such as silicone or Polyurethane, and may have a super-elastic Nitinol ring to reinforce closure. FIG. 6C illustrates a proximal side view of the end 640 with the discontinuity 642.

As shown in FIG. 6B, a shunt delivery component 2 can extend through the discontinuity 642 during an implantation procedure. Such a delivery component 2 may include a guidewire, a stylet, or a portion of another puncture system. Embodiments of a shunt delivery component 2 are disclosed in in U.S. Prov. No. 63/446,064, filed on Feb. 16, 2023, and U.S. Ser. No. 18/443,455, filed on Feb. 16, 2024, the entireties of which are incorporated by reference, herein. During an implantation procedure, multiple shunt delivery components 2 may be inserted and removed through the end 640 via the discontinuity 642.

For example, the discontinuity 642 allows for a puncture-system-type delivery component 2 to pass through the inner lumen of the shunt body 610 (and/or other portions of the shunt, such as the distal region and inlet (not shown)). In this example, the delivery component 2 can puncture the dura 10 prior to placement of the shunt.

FIG. 6B shows a cross-sectional view of the delivery component 2 passing through the discontinuity 642. The discontinuity 642 may be located between flexible leaves or flaps. Such leaves or flaps can be reinforced, for example, such as with super-elastic Nitinol. When the delivery component 2 is removed from the discontinuity 642, the end 640 seals back up due to the material included in the regions (or structure reinforcing the regions) of the end 640 surrounding the discontinuity 642. Such materials or reinforcing structures keep the discontinuity 642 closed after removal of the delivery component 2. Closure of the discontinuity 642 prevents CSF flow out of the end 642 and prevents blood regress back in to the shunt body 610, for example, at any of the expected range of CSF head pressure (e.g., 0 to 50 cmH2O).

Figure 7A:
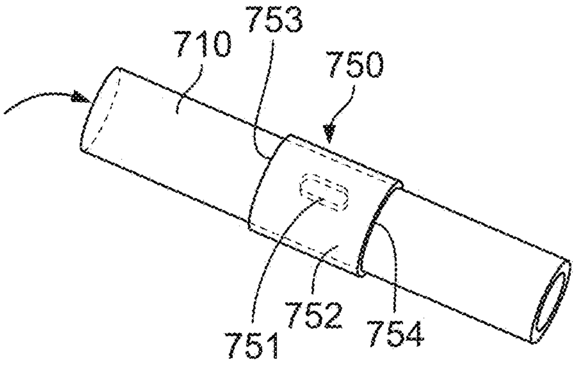
FIGS. 7A, 7B, 7C, 7D, and 7E illustrate CSF shunts with different configurations for flow regulation, according to embodiments.
Figure 7B:
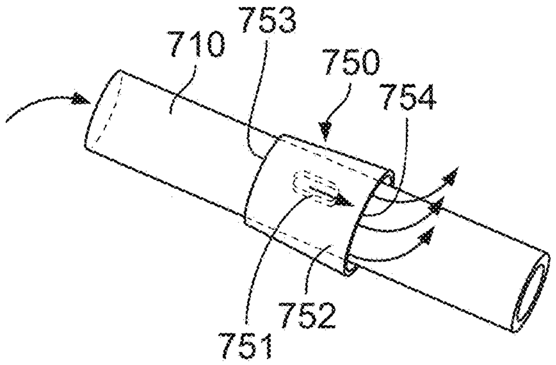
Figure 7C:
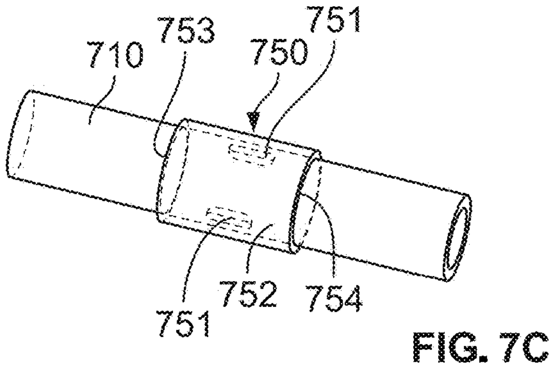

FIGS. 7A, 7B, 7C, 7D, and 7E illustrate embodiments of a shunt body 710 with a regulator 750 that regulates CSF flow through the shunt body 710. The shunt body 710 may be similar to other shunt bodies described herein. In each of FIGS. 7A-7E, the regulator 750 further includes a sleeve 752 that overlaps the shunt body 710. The inner diameter of the sleeve 752 may be less than the outer diameter of the shunt body 710. The sleeve 752 overlaps at least a portion of one or more discontinuities 751 (two shown in FIG. 7C) in the shunt body 710. As shown, the discontinuity 751 is an aperture although a slit (or multiple slits) is contemplated. In FIGS. 7A-7C, the discontinuity 751 is shown in broken line, as it is underneath the sleeve 752 and otherwise not visible from the exterior of the shunt. According to an embodiment, at least a portion of the discontinuity 751 is not overlapped by the sleeve 752 and is visible from the exterior of the shunt. The sleeve 752 may be partial and not extend around the entire circumference of the shunt body 710. There may be multiple sleeves 752 that do not extend around the circumference of the shunt body 710 in the same axial region of the shunt.

The sleeve 752 includes a distal end 753 and a proximal end 754. The sleeve 752 may be placed at any suitable location along the shunt body 710, as long as the sleeve 752 is to be located within the venous system when the shunt is in situ. It may be possible to have multiple sleeves 752 and corresponding discontinuities 751. At least a portion of either the distal end 753 or the proximal end 754 may be coupled (e.g., sealed, attached, bonded) to the shunt body 710. At least a portion of the other end may not be coupled to the shunt body 710 and may be a free end. In an embodiment, a portion of the distal end 753 or the proximal end 754 is coupled to the shunt body 710 in some areas and not coupled in other areas. In an embodiment, the distal end 753 is coupled with the shunt body 710 and the proximal end 754 is a free end. This embodiment is shown in FIGS. 7A-7E. In an embodiment, the proximal end 754 is coupled to the shunt body 710 and the distal end 753 is the free end.

The sleeve 752 may include a semi-elastic or elastic material (e.g., durometer of 15 A to 90 A, such as approximately 50 A). This material can be implanted in the sleeve 752 and may be the same or different from the material of the shunt body 710. Examples of a material included in the sleeve 752 include high PTFE loaded, low to high durometer urethanes, low or high durometer silicones, a straight PTFE sleeve, elastomeric, and/or the like. In addition, the sleeve material maybe coated with antibacterial and or anticlotting materials, e.g Heparin or such. The sleeve may be a composite in that the underlayer material overlays on the shunt and the outer material contacts the blood.

Figure 7D:
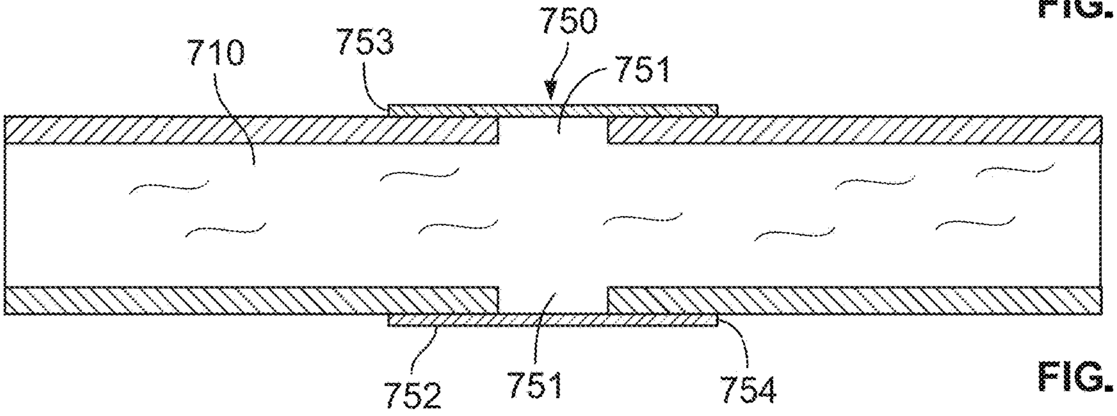
Figure 7E:
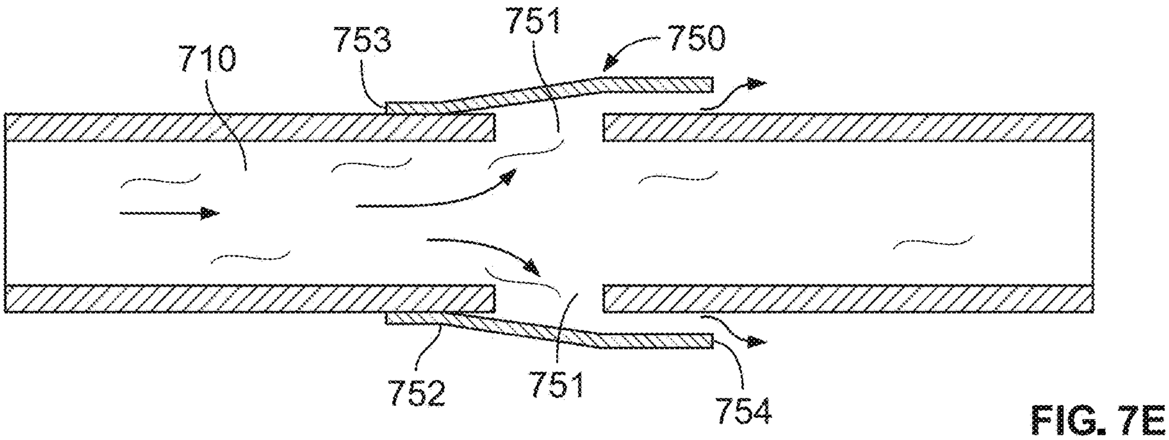
Figure 8A:
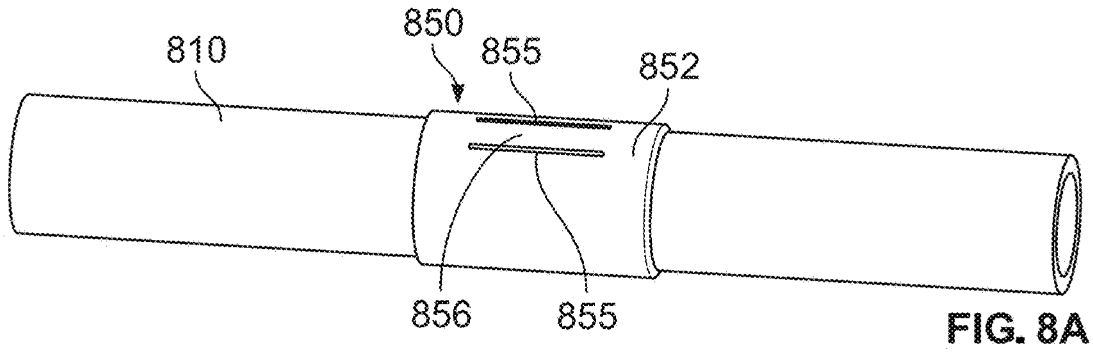
FIGS. 8A, 8B, 8C, 8D, and 8E illustrate different views of a CSF shunt body and a regulator, according to embodiments.
Figure 8B:
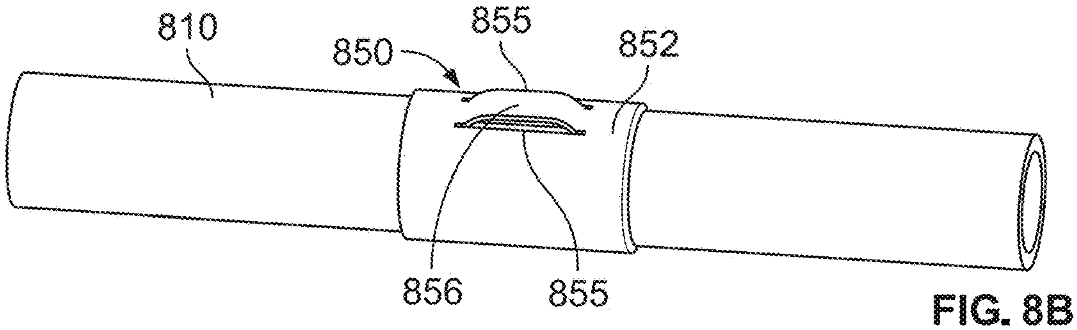
Figure 8C:
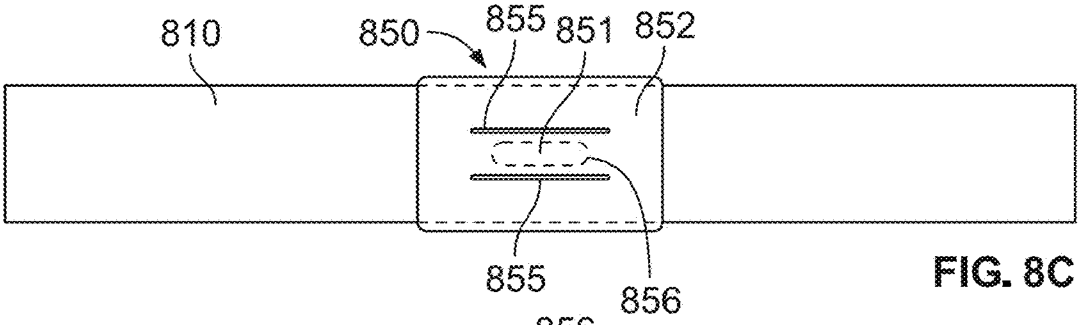
Figure 8D:
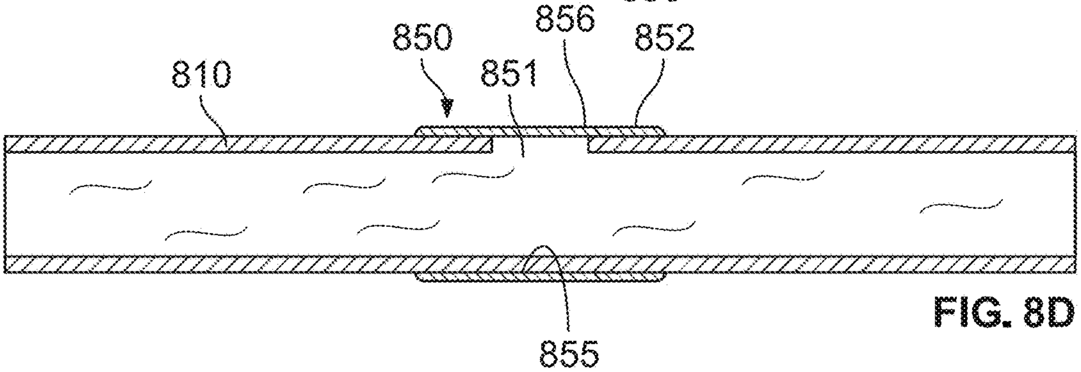
Figure 8E:
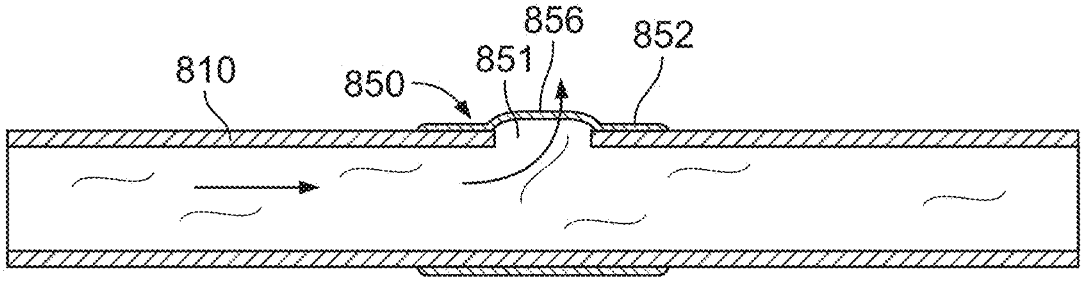
Figure 9A:
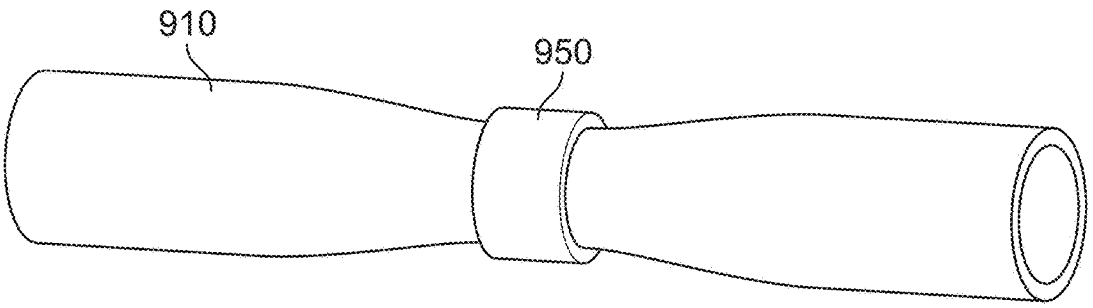
FIGS. 9A, 9B, 9C, and 9D illustrate a CSF shunt body and a constrictor for flow regulation, according to embodiments.
Figure 9B:
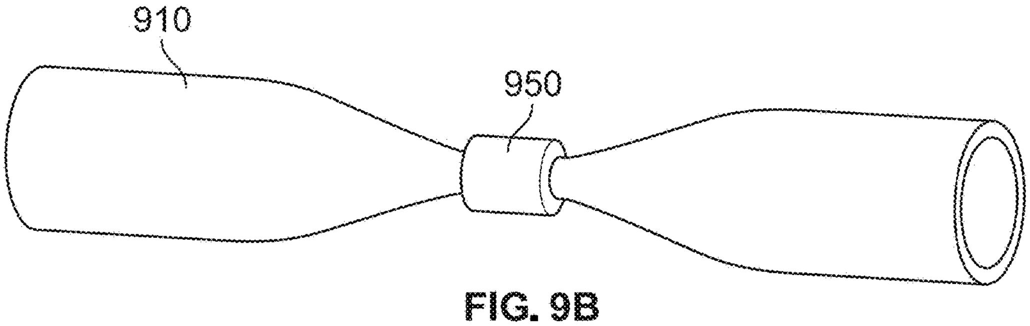
Figure 9C:
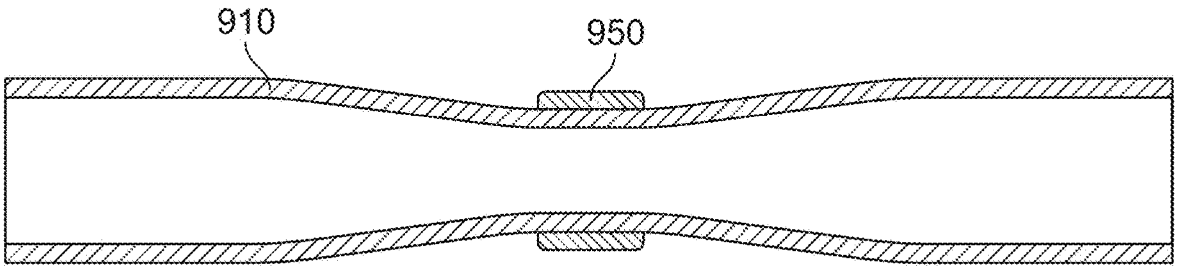
Figure 9D:
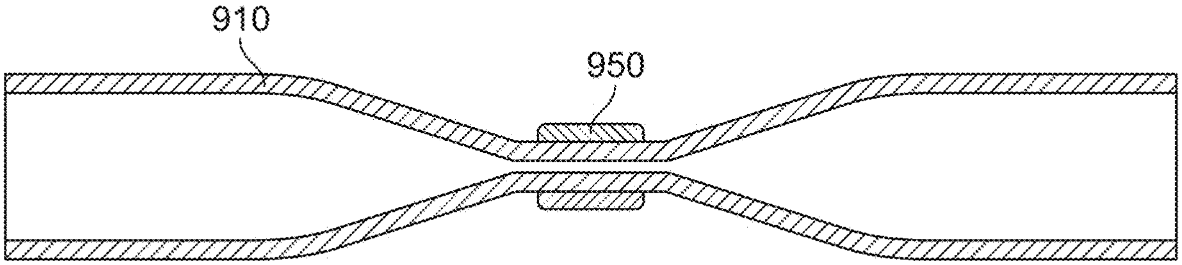

As shown, for example, in FIG. 7D, the distal end 753 is coupled to the shunt body 710. The proximal end 754 is a free end. When the CSF pressure is sufficiently low, the length of the sleeve 752 lies flat or flush against the shunt body 710 covering at least a portion of the discontinuity 751. The elastic nature of the sleeve 752 facilitates maintaining the covering of at least a portion of the discontinuity 751. As shown in FIG. 7E, at a predetermined CSF head pressure(s), the CSF pressure causes the sleeve 752 to expand outwardly. The free end (as shown, the proximal end 754) separates from the shunt body 710, thus allowing CSF to flow out between the shunt body 710 and the sleeve 752 and in to the venous system. When the CSF pressure drops below a predetermined level, the sleeve 752 can return to its position with no separation between the free end and the shunt body 710.

FIGS. 8A, 8B, 8C, 8D, and 8E illustrate different views of a shunt body 810 and a regulator 850, according to embodiments. The shunt body 810 may be similar to other shunt bodies disclosed herein. The regulator 850 includes a discontinuity 851 and a sleeve 852. The discontinuity 851 may be similar to other discontinuities disclosed herein. The sleeve 852 may be similar to the sleeve 752. As shown, both the distal and proximal ends of the sleeve 852 are coupled to the shunt body 810, although one or both of the ends or portions thereof may not be coupled. The sleeve 852 includes one or more discontinuities 855. As shown, the sleeve 852 includes two discontinuities 855 that form a flap 856. The flap 856 overlaps the discontinuity 851. When the CSF pressure is below a predetermined level, the flap 856 lies flat or flush over the discontinuity 851. When the CSF pressure exceeds the predetermined level, the CSF causes the flap 856 to expand, thereby allowing CSF to flow out of the discontinuities 855. When the CSF pressure drops below the predetermined level, the flap returns to being flush or flat over the discontinuity 851. The sleeve 852 need not have a plurality of discontinuities, and can be implemented with only one discontinuity.

FIGS. 9A, 9B, 9C, and 9D illustrate a shunt body 910 and a constrictor 950 (a type of regulator) for flow regulation, according to embodiments. The shunt body 910 may be similar to other shunt bodies described herein. The constrictor 950 may be similar to the sleeves 752, 852 described herein. The inner diameter of the constrictor 950 may be less than the outer diameter of the shunt body 910. The constrictor 950 may apply a radial force to the exterior of the shunt body 910, constricting the lumen of the shunt body 910, thereby regulating the flow of CSF. At higher predetermined pressures, the constrictor 950 may expand to a larger diameter, allowing fluid to pass through the lumen of the shunt body 910.

Figure 10A:
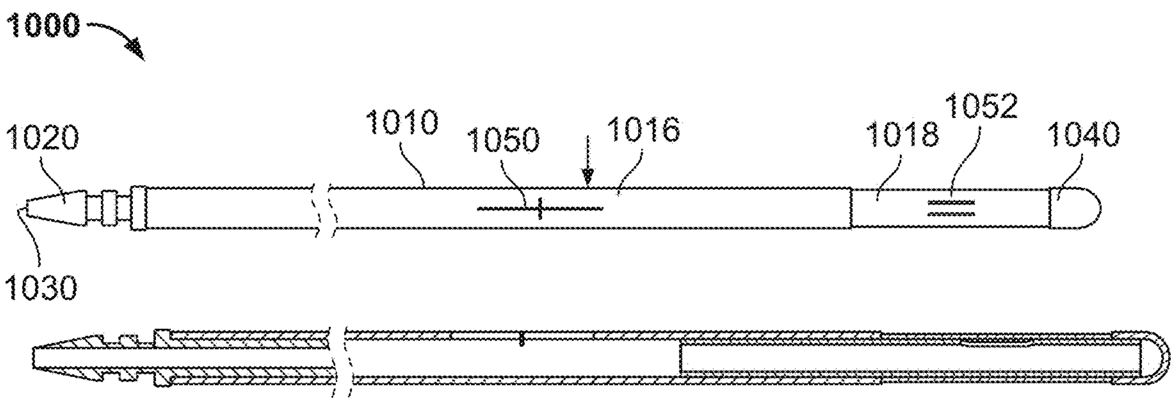
FIGS. 10A, 10B, and 10C illustrate different views of a CSF shunt, according to embodiments.
Figure 10B:
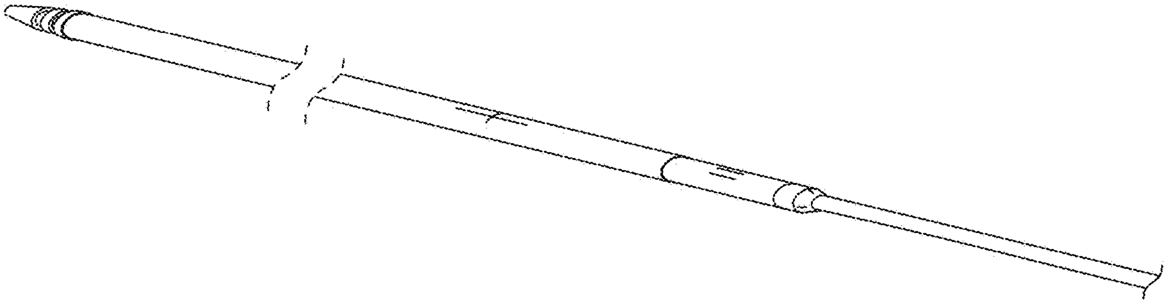
Figure 10C:
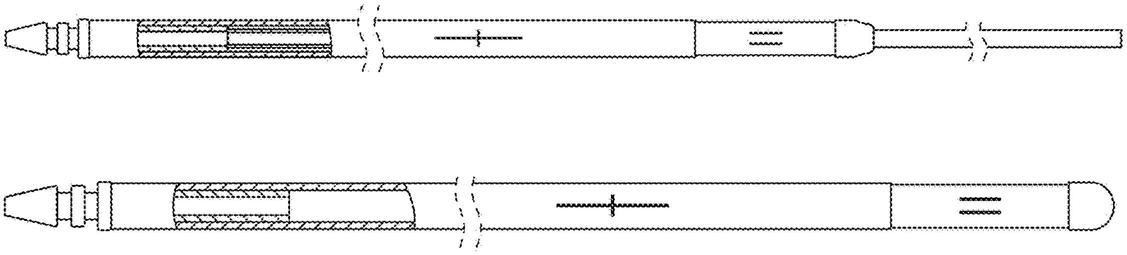

FIGS. 10A-10C illustrate different views of an exemplary CSF shunt 1000. FIG. 10A depicts both a lateral view and a cross-sectional view. The CSF shunt 1000 may be similar to other shunts described herein, including components thereof. The CSF shunt 1000 includes a distal region 1020 (e.g., similar to distal region 1120) including an inlet 1030

(e.g., similar to inlet 1130). The distal region 1020 is coupled to a shunt body 1010 (e.g., similar to other shunt bodies described herein). The shunt 1000 further includes a closed end 1040 (e.g., similar to other closed ends described herein). The shunt body 1010 includes a first region 1016 (e.g., similar to other first regions described herein) and a second region 1018 (e.g., similar to other second regions described herein). The first region 1016 includes a regulator 1050 (e.g., similar to other regulators described herein). The regulator 1050 is shown as a slit-type regulator. The second region 1018 includes a regulator 1052 (e.g., similar to other regulators described herein). The regulator 1052 as shown is similar to a portion of the regulator 850 described with respect to FIGS. 8A-8E. The regulator 1052 includes two discontinuities (similar to discontinuities 855) that define a flap (similar to flap 856). The flap expands and contracts, thereby regulating CSF flow through the lumen of the shunt body 1010 and out of the regulator 1052.

As discussed, multiple regulators may be included in a shunt, such as two or more of the regulators disclosed herein. One of the regulators may be a primary regulator and may open to allow for relatively small amounts of CSF flow at relatively low CSF pressure. A secondary regulator may open at higher CSF pressure to further increase the CSF flow through the shunt. The pressure to open the first regulator may be lower than the pressure to open the second regulator. Further regulators may be designed to open at different predetermined pressures.

An exemplary regulator(s) may stop blood regress by constricting and sealing shut at a predefined pressure (e.g., between approximately 1 to 12 cmH2O, such as 7 cmH2O). A given constricting/sealing pressure may be selected according to a patient's diagnosis. For example, patients who are diagnosed with NPH may need the predetermined sealing pressure to be lower to reduce effects of hydrocephalus, whereas patients with IIH may need the predetermined sealing pressure to be higher.

Figure 12A:
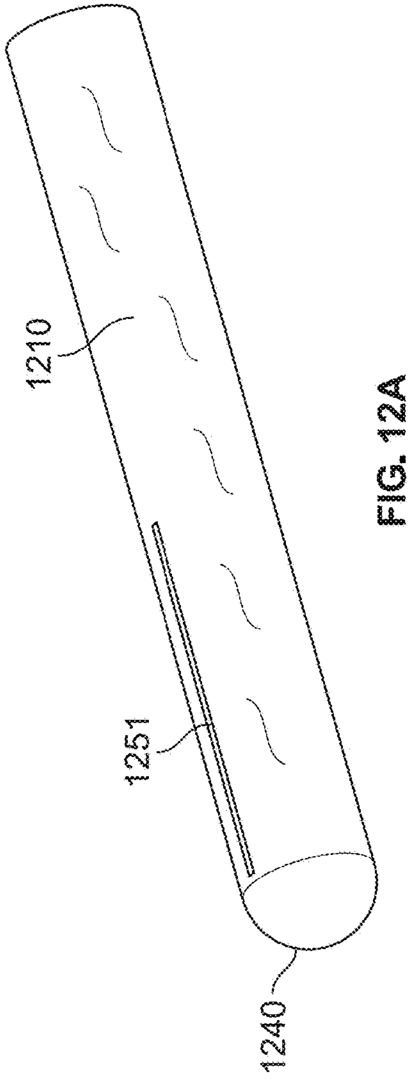
FIGS. 12A, 12B, and 12C illustrate a portion of a CSF shunt with a flow regulator, according to embodiments.
Figure 12B:
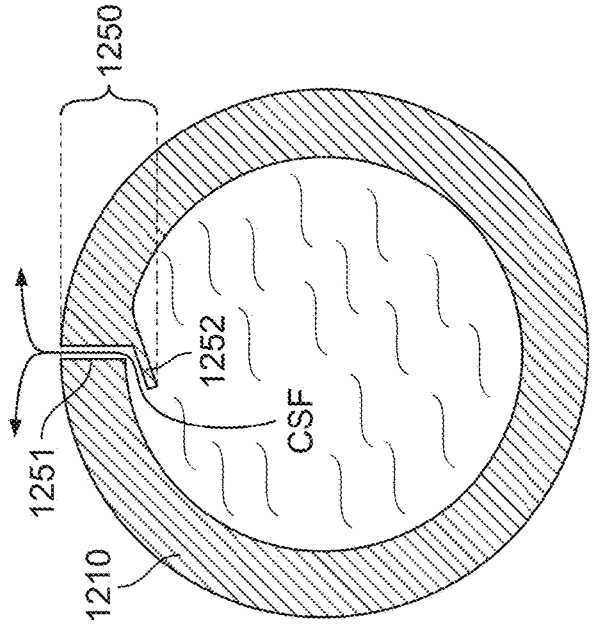
Figure 12C:
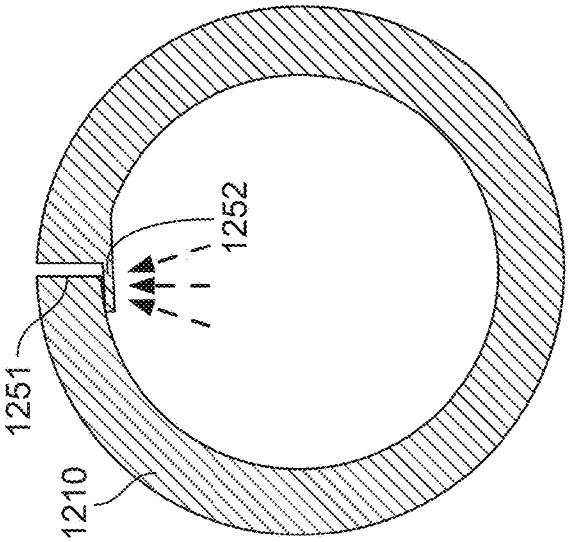

FIGS. 12A-12C show an embodiment of a portion of a CSF shunt with a regulator 1250. FIG. 12A shows a perspective view of the portion of the CSF shunt, including a shunt body 1210, a closed end 1240, and the regulator 1250. The shunt body 1210 and/or closed end 1240 may be similar to other such components described herein (e.g., shunt body 1110 and closed end 1140). FIGS. 12B and 12C show cross-sectional views of the shunt body 1210 and the regulator 1250 in different states.

The regulator 1250 (which may be in addition to other regulators) includes a discontinuity 1251 in the sidewall of the shunt body 1210. The discontinuity may be shaped, be configured, or function in a similar manner as other discontinuities described herein (e.g., multiple discontinuities, various shapes, etc.). The regulator 1250 further includes a flow restrictor 1252. In the depicted embodiment, the flow restrictor 1252 is a flap. The flow restrictor 1252 may extend or be part of the inner surface of the sidewall of the shunt body 1210. The flow restrictor 1252 may extend underneath and across the discontinuity 1251. The flow restrictor 1252 may extend along the axial length of the discontinuity 1251 or only a portion thereof. The flow restrictor 1252 may be formed of or include the same material(s) as the shunt body 1210 or different material(s).

As shown in FIG. 12B, when there is lower pressure in the CSF, the flow restrictor 1252 is open, thereby potentially allowing the CSF to flow through the discontinuity 1251. As shown, the discontinuity 1251 is open, but it may be closed if the CSF fluid pressure is sufficiently low. As shown in FIG. 12C, when there is higher pressure in the CSF, the flow restrictor 1252 closes, thereby obstructing the CSF from flowing through the discontinuity 1251. In the case of a flap, the length, thickness, width of the flow restrictor 1252 can be adjusted to increase or decrease its obstructive effects at different pressures of the CSF. In such a way, it may be possible to limit or stop the flow of the CSF fluid through the regulator 1250 when the CSF pressure exceeds a given threshold. Further, the obstructive effect of the flow restrictor 1252 may be variable, by progressively narrowing the inlet through the flow restrictor 1252 and the other portions of the inner sidewall of the shunt body 1210, and when the CSF pressure is sufficiently high, the flow restrictor 1252 closes altogether. This may inhibit over-drainage of CSF when the pressure spikes or increases beyond a given threshold.

The flow restrictor 1252 may have one or more apertures. The aperture(s) may align partially or completely with the discontinuity 1251. The apertures in the flow restrictor 1252 may function such that CSF can still flow through the discontinuity 1251 even when the CSF pressure is particularly high, but CSF can only flow through the regulator 1250 at a lower rate because it will only be able to flow through the apertures in the flow restrictor 1252, even with the flow restrictor 1252 is in the closed state.

Figure 13:
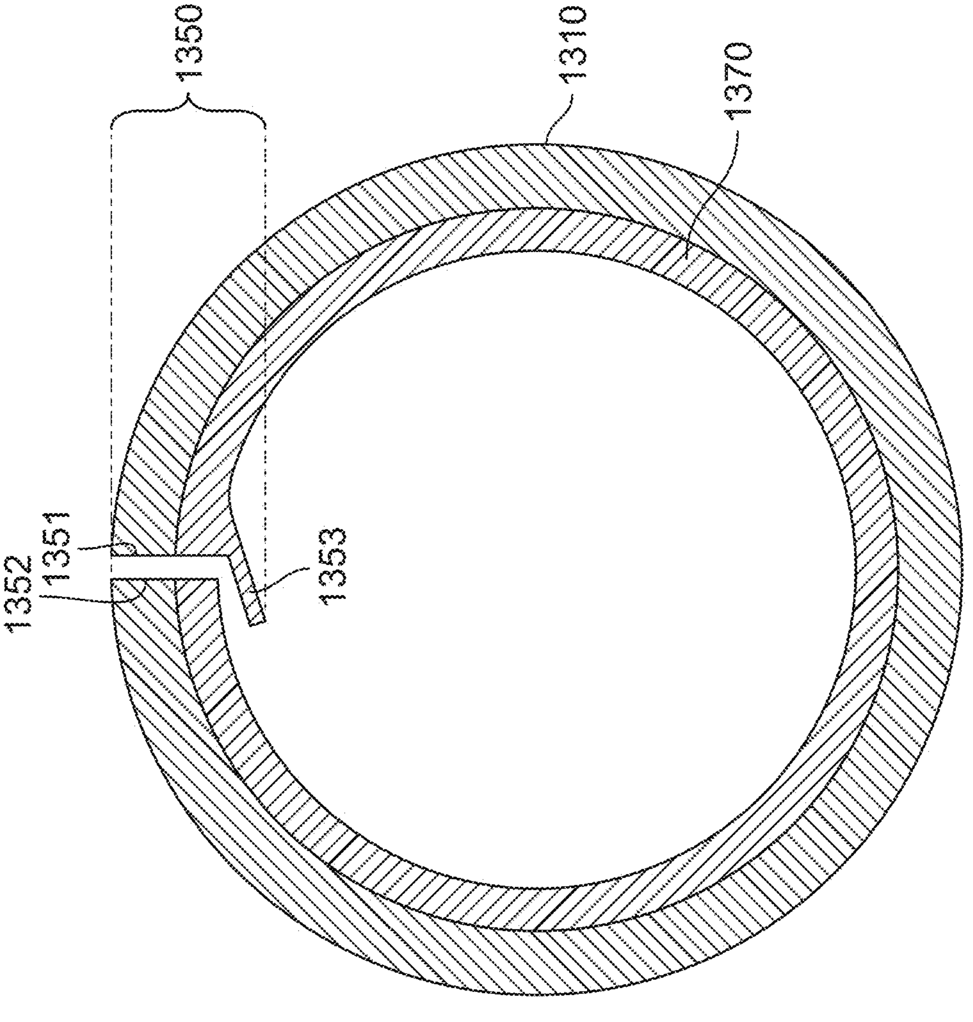
FIG. 13 illustrates a cross-sectional view of a portion of a CSF shunt with a flow regulator.

FIG. 13 is similar to FIG. 12B. FIG. 13 shows a cross-sectional view of a shunt body 1310, a flow regulator 1350, and an insert 1370. The shunt body 1310 includes a discontinuity 1351, similar to the discontinuity 1251 in the shunt body 1210. Further in FIG. 13, the insert 1370 is exemplarily depicted as being concentrically arranged within the shunt body 1310. The insert 1370 may be more rigid than the shunt body 1310. The insert 1370 may be inserted into the shunt body 1310 during manufacturing, or the insert 1370 may be integrated with the shunt body 1310 at the time that the shunt body 1310 and the insert 1370 are formed. Or the shunt body 1310 may be formed over the insert 1370.

The insert 1370 includes a discontinuity 1352. The discontinuity 1352 may be elongate or may be similar to other types of discontinuit(ies) described herein and may be formed in similar ways. The discontinuity 1352 may extend along and underneath at least a portion of the discontinuity 1351. In such a way, the discontinuity 1351 and the discontinuity 1352 are partially or completely aligned, such that under certain conditions, CSF can flow through the discontinuities 1351, 1352. The discontinuity 1352 may behave, function, or perform like other discontinuities described herein (e.g., open under greater pressure, close under lesser pressure, etc.). The discontinuity 1352 may remain open through a range of expected CSF pressures, and this may be different from the discontinuity 1351, which may, in contrast, both open and close based on CSF pressure.

Further, a flow restrictor 1353 is also shown in FIG. 13. The flow restrictor 1353 may be similar to the flow restrictor 1252. Instead of aligning (at least partially) with the discontinuity 1351 in the shunt body 1310, the flow restrictor 1353 aligns (at least partially) with the discontinuity 1352 in the insert 1370. In the case that the discontinuities 1351, 1352 align, then the flow restrictor 1353 also would align with the discontinuity 1351. The regulator 1350 includes the discontinuity 1351, the discontinuity 1352, and the restrictor 1353 in the depicted embodiment.

Figure 14A:
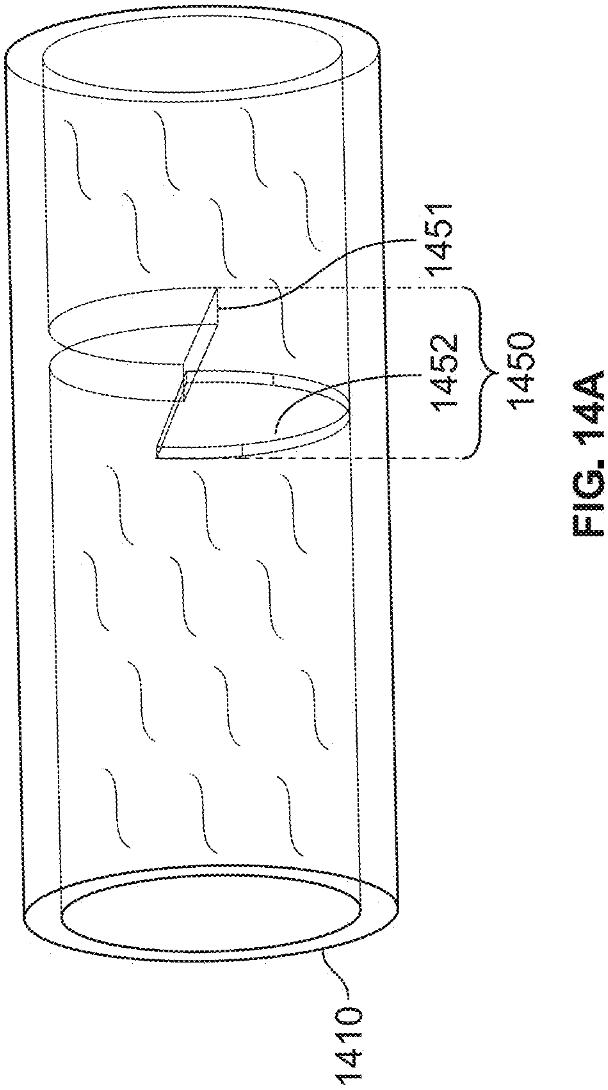
FIGS. 14A, 14B, and 14C illustrate different views of a CSF shunt body and a regulator, according to embodiments.
Figure 14C:
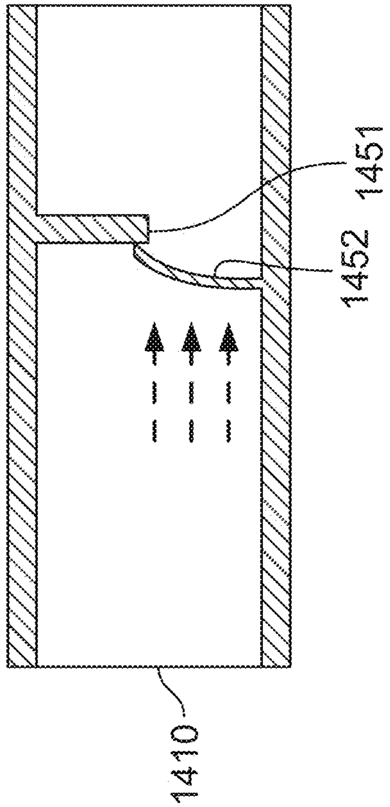
Figure 14B:
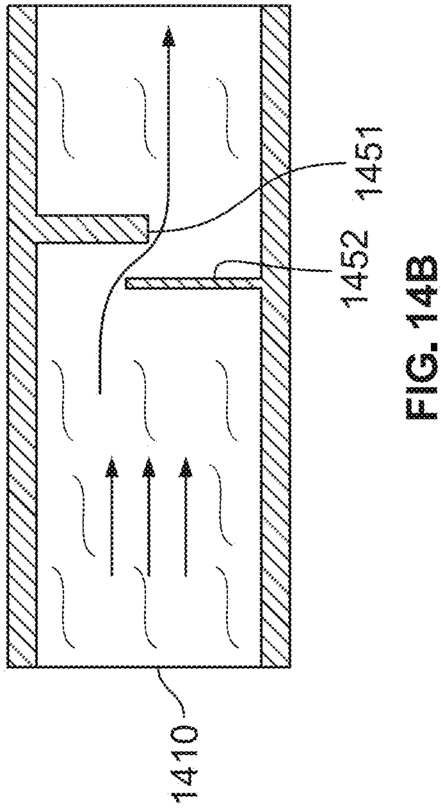

FIGS. 14A-14C show different views of a portion of a shunt body 1410 and a regulator 1450, according to embodiments. FIG. 14A is a perspective view with transparency, thereby showing the inner lumen of the shunt body 1410 and components therein. FIG. 14B is axial cross-sectional view of FIG. 14A with relatively low CSF pressure. FIG. 14C is the same axial view as FIG. 14B, except that CSF pressure is relatively high.

The shunt body 1410 may be similar to other shunt bodies described herein. The regulator 1450 (which may be in addition to other regulators) is arranged within the lumen of the shunt body 1410. The regulator 1450 includes a rigid portion 1451 and a flow restrictor 1452. The rigid portion 1451 may be substantially rigid in that it may not substantially deflect or deform under a range of expected CSF pressures (e.g., the rigid portion 1451 will not substantially deform or deflect at the maximum expected CSF pressure). The rigid portion 1451 may be integral with the shunt body 1410 or may be a separate piece. The rigid portion 1451 may be thicker than the flow restrictor 1452 along the axial dimension. The rigid portion 1451 may be a half-moon extending halfway through the lumen of the shunt body 1410 (as shown), or may have other shapes (e.g., a toroid, a half moon that extends less or more than half way through the lumen of the shunt body 1410, a wall extending through the thickness of the lumen of the shunt body 1410 with a number of aperture(s), or the like). Some or all of such aperture(s) may or may not be partially or completely covered by the flow restrictor 1452 when it is closed, as will be further described.

The flow restrictor 1452 may also be positioned in the lumen of the shunt body 1410 and upstream of the rigid portion 1451. The flow restrictor 1452 may be a relatively flexible component, as compared to the rigid portion 1451. The flow restrictor 1452 may be elastic and may have memory. The flow restrictor 1452 may have various shapes, such as the various shapes described with respect to the rigid portion 1451. The flow restrictor 1452 may be connected to the shunt body 1410 along the entire lower and lateral perimeter (e.g., the "U" shape shown in FIG. 14A) of the flow restrictor 1452, or only a portion of the lower and lateral perimeter of the flow restrictor 1452 may be connected to the shunt body 1410. For example, an upper region of the lower and lateral periphery of the flow restrictor 1452 may not be connected to the shunt body 1410, while a lower region of the lower and lateral periphery of the flow restrictor 1452 may be connected to the shunt body 1410.

At lower CSF pressure, the flow restrictor 1452 may remain in its default position (e.g., its relaxed position), an example of which is shown in FIG. 14B. As CSF pressure increases, the flow restrictor 1452 may flex towards the rigid portion 1451. As CSF pressure continues to increase, the flow restrictor 1452 may come into contact with the rigid portion 1451 or at least close the distance towards the rigid portion 1451. The flow restrictor 1452 may function similarly to the flow restrictor 1252, except that the flow restrictor 1452 may close or narrow the distance to the rigid portion 1451, whereas the flow restrictor 1252 may close or narrow the distance to the inner sidewall of the shunt body 1410. As with the flow restrictor 1252, the flow restrictor 1452 may also include one or more apertures that allow some CSF flow (e.g., a reduced CSF flow) through the lumen of the shunt body 1410 even under conditions when the CSF pressure is sufficiently high to deflect the flow restrictor 1452 such that it contacts the rigid portion 1451.

FIGS. 15A-15D illustrate embodiments of stiffening members 1580*a*-1580*d* (collectively, stiffening member 1580) that are positioned within the lumen of the shunt body 1510. The stiffening member 1580 may impart a stiffness to the CSF shunt (e.g., the stiffening member 1580 may be stiffer than the shunt body 1510 (or stiffer than a region of the shunt body 1510 that abuts at least a portion of the stiffening member 1580). The stiffening member 1580 may be inserted into the shunt body 1510 during manufacturing. Or the stiffening member 1580 may be formed integrally with the shunt body 1510, or the shunt body 1510 may be formed over the stiffening member 1580. Also shown is a closed end 1540, which may be similar to the other closed ends described herein (e.g., closed end 1140).

The stiffening member 1580 may be located in a region of a regulator 1550 (which may be similar to other regulators described herein). The stiffening member 1580 may allow flow of CSF fluid through the lumen of the shunt body 1510 and through the regulator 1550.

Figure 15A:
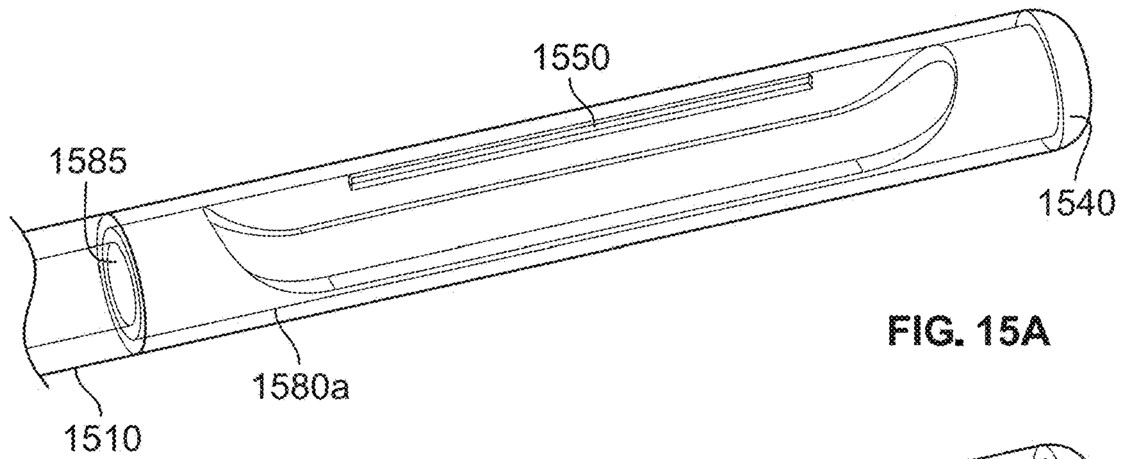
FIGS. 15A, 15B, 15C, and 15D illustrate embodiments of an insert in a lumen of a CSF shunt body, according to embodiments.

FIG. 15A shows a stiffening member 1580*a* in which an upper region is open. The stiffening member 1580*a* may have a distal aperture 1585 to allow the flow of CSF towards the regulator 1550. The CSF can then flow through the open, upper region of the stiffening member 1580*a* and through the regulator 1550 under certain conditions (such as the ones described herein).

Figure 15B:
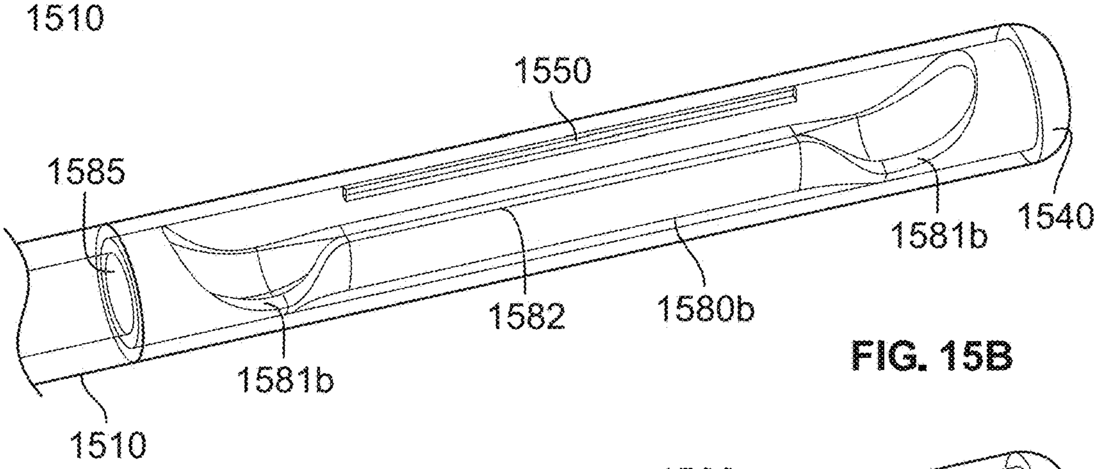

FIG. 15B shows a stiffening member 1580*b* which may be similar to the stiffening member 1580*a*, but the stiffening member 1580*b* has a plurality of openings 1581*b* in its upper region. The stiffening member 1580*b* further includes a closed region 1582 between the openings 1581*b*. There may be some space within the inner lumen of the shunt body 1510 between the closed region 1582 and the regulator 1550. The closed region 1582 can open up more of the inner diameter of the shunt wall so that CSF pressure can act on it and open the discontinuity in a desired manner.

Figure 15C:
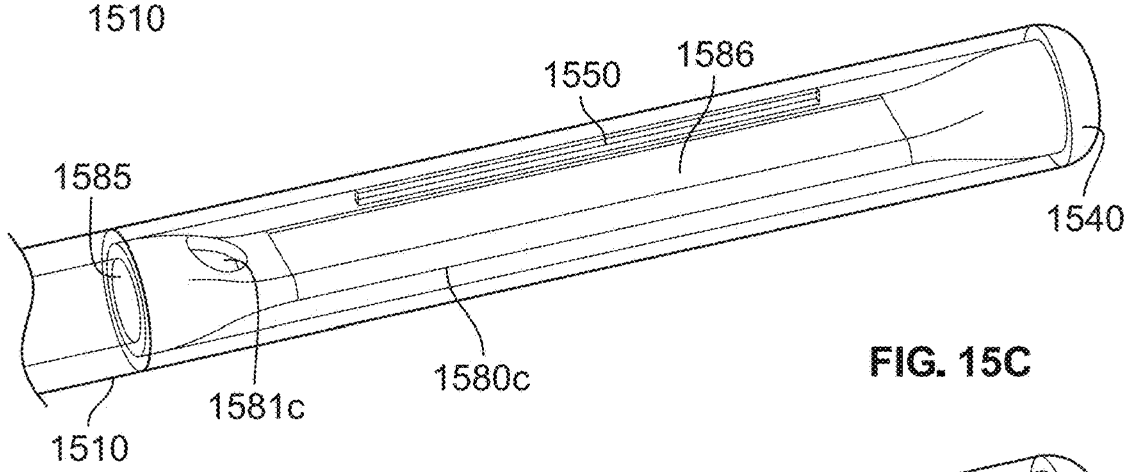

FIG. 15C shows a stiffening member 1580*c*, which has an opening 1581*c* in a distal region proximate the opening 1585. In the illustrated embodiment, an elongate region 1586 extends from near the opening 1581*c* and towards the proximal end of the shunt body 1510. There may be no opening or lumen within the elongate region 1586. The elongate region 1586 may be centered within the inner diameter of the shunt body 1510, and may allow for CSF pressure to act on the full inner circumference of the shunt body 1510 without substantially affecting the flow of fluid.

Figure 15D:
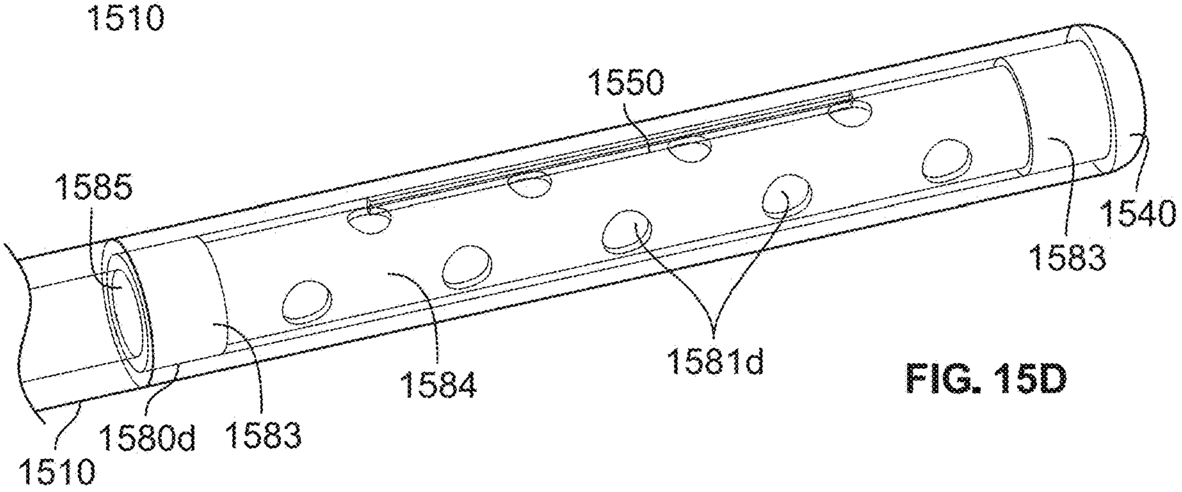

FIG. 15D shows a stiffening member 1580*d*, which in regards may be similar to the aforementioned stiffening members. The stiffening member 1580*d* has region(s) of larger outer diameter 1583 and region(s) of smaller outer diameter 1584. In the region 1584, there may be opening(s) 1581*d*. The smaller diameter region 1584 may not touch the inner diameter of the shunt body 1510, which allows for all of the fluid pressure to act on the inner circumference of the shunt body 1510.

The stiffening member 1580 may reduce the risk of the CSF shunt kinking and/or bending after or during implantation. The stiffening member 1580 may tend to straighten the shunt body 1510 in the region where the stiffening member 1580 is present. The stiffening member 1580 may be positioned in a region proximate to or coextensive with the regulator 1550 to prevent undue kinking and/or bending in the region of the regulator 1550. In regions where the shunt body 1510 does not contain the stiffening member 1580, the shunt body may maintain its flexibility, which may be advantageous for the implantation procedure.

According to embodiments, a CSF shunt can contain an emergency shutoff ring. This ring could be a Nitinol actuator ring that is activated by radio frequency to heat the ring, such that it constricts (or closes altogether) to act as emergency stop gate. The austenite finish (AF) temperature can be set around 40 C to 50 C to activate and constrict the ring. In contrast, the ring could be actuated to increase in diameter to open up a segment of the shunt and/or allow for increased CSF flow through the shunt. The Nitinol may be activated. Nitinol can "remember" its original shape (SM)—this when deformed at a low temperature, it can return to its original form upon heating above its transformation temperature, i.e., Af.

According to embodiments, the shunt body and regulator region can be excited by vibration, such as ultrasonic waves. This could allow the shunt to be vibrated in-vivo by, for example, a hand-held device outside of the patient and cleared of build ups on the shunt and/or in and around the regulator. Certain section(s) could contain embedded particles, molecular elements, and or components that are excited by particular radio frequencies.

The shunt could be longer allowing the proximal end and regulator section to reside in a larger vessel such as the Iliac vein and/or femoral vein and have a mechanically/electrically controllable valve. The mechanically/electrically controllable valve could allow a physician to reprogram the desired valve flow rate or reset the valve using a hand-held controller.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope. Therefore, it is intended that the novel techniques not be limited to the particular techniques disclosed.

The invention claimed is:

1. A cerebrospinal fluid (CSF) shunt, comprising:

an inlet configured to receive CSF from a spinal intradural space in a patient;

a shunt body with a sidewall and a lumen within the sidewall, wherein the shunt body is configured to extend through an interstitial space and a vein wall, wherein the lumen is in fluid communication with the inlet; and a regulator outside of the lumen, wherein the regulator is configured to regulate a flow of the CSF from the inlet by passing a regulated portion of the CSF from the lumen and into a venous system of the patient, wherein:

the sidewall of the shunt body includes a first region including a first material and a second region including a second material;

at least one of the first material has a lower durometer than the second material, or the first region has a smaller inner diameter than the inner diameter of the second region;

the regulator is in the first region; and no regulator is in the second region.

2. The CSF shunt of claim 1, wherein the regulator comprises a slit regulator in the sidewall of the shunt body.

3. The CSF shunt of claim 1, wherein the first material has a lower durometer than the second material.

4. The CSF shunt of claim 3, wherein the regulator includes a non-stick material.

5. The CSF shunt of claim 1, wherein the first region has a smaller inner diameter than the inner diameter of the second region.

6. The CSF shunt of claim 1, wherein the first material has a lower durometer than the second material and the first region has a smaller inner diameter than inner diameter of the second region.

7. A cerebrospinal fluid (CSF) shunt, comprising:

an inlet configured to receive CSF from a spinal intradural space in a patient;

a shunt body with a sidewall and a lumen within the sidewall, wherein the shunt body is configured to extend through an interstitial space and a vein wall, wherein the lumen is in fluid communication with the inlet; and a regulator outside of the lumen, wherein the regulator is configured to regulate a flow of the CSF from the inlet by passing a regulated portion of the CSF from the lumen and into a venous system of the patient, wherein:

the regulator comprises a first regulator and a second regulator;

the sidewall of the shunt body includes a first region including a first material and a second region including a second material;

at least one of the first material has a lower durometer than the second material, or the first region has a smaller inner diameter than the inner diameter of the second region; and the first regulator is in the first region; and the second regulator is in the second region.

8. The CSF shunt of claim 7, wherein the first material has a lower durometer than the second material.

9. The CSF shunt of claim 8, wherein the first regulator and the second regulator include a non-stick material.

10. The CSF shunt of claim 7, wherein the first region has a smaller inner diameter than the inner diameter of the second region.

11. The CSF shunt of claim 7, wherein the first material has a lower durometer than the second material and the first region has a smaller inner diameter than the inner diameter of the second region.

12. The CSF shunt of claim 7, wherein the first regulator and the second regulator regulate differently from each other.

13. A cerebrospinal fluid (CSF) shunt, comprising:

an inlet configured to receive CSF from a spinal intradural space in a patient;

a shunt body with a sidewall and a lumen within the sidewall, wherein the shunt body is configured to extend through an interstitial space and a vein wall, wherein the lumen is in fluid communication with the inlet; and a regulator outside of the lumen, wherein the regulator is configured to regulate a flow of the CSF from the inlet by passing a regulated portion of the CSF from the lumen and into a venous system of the patient, wherein the regulator comprises at least one discontinuity in the sidewall of the shunt body and a sleeve exterior to an outer surface of the sidewall of the shunt body, wherein the sleeve overlaps the at least one discontinuity.

14. The CSF shunt of claim 13, wherein sleeve includes an end coupled to the shunt body and an end at least partially not coupled to the shunt body.

15. The CSF shunt of claim 14, wherein the end at least partially not coupled to the shunt body is entirely not coupled to the shunt body.

16. The CSF shunt of claim 13, wherein the sleeve comprises at least one discontinuity.

17. A cerebrospinal fluid (CSF) shunt, comprising:

an inlet configured to receive CSF from a spinal intradural space in a patient;

an outlet configured to provide the CSF into a venous system in the patient;

a shunt body with a sidewall and a lumen within the sidewall, wherein the shunt body is configured to extend through an interstitial space and a vein wall, wherein the lumen is in fluid communication with the inlet and the outlet, such that a flow of the CSF flows between the inlet and the outlet; and a regulator configured to vary at least one of the size or the shape of the outlet to regulate the flow of the CSF fluid, wherein:

the shunt body comprises a first region including a material having a first durometer and a second region including a material having a second durometer less than the first durometer; and the outlet is formed at least partially by the second region.

18. A cerebrospinal fluid (CSF) shunt, comprising:

an inlet configured to receive CSF from a spinal intradural space in a patient;

an outlet configured to provide the CSF into a venous system in the patient;

a shunt body with a sidewall and a lumen within the sidewall, wherein the shunt body is configured to extend through an interstitial space and a vein wall, wherein the lumen is in fluid communication with the inlet and the outlet, such that a flow of the CSF flows between the inlet and the outlet; and a constrictor positioned outside of the shunt body, wherein an inner diameter of the constrictor is less than an outer diameter of the shunt body, wherein the constrictor is elastic and regulates the flow of the CSF.

* * * * *